United States Patent
Levin et al.

(10) Patent No.: US 8,323,503 B2
(45) Date of Patent: Dec. 4, 2012

(54) USER INTERFACE PROCESSING DEVICE

(75) Inventors: Roland Levin, San Ramon, CA (US); Martin Joseph Crnkovich, Walnut Creek, CA (US); Fei Wang, Contra Costa, CA (US); Michael Emmanuel Kotsos, Walnut Creek, CA (US); Gregg Eric Fuhriman, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1122 days.

(21) Appl. No.: 12/137,375

(22) Filed: Jun. 11, 2008

(65) Prior Publication Data

US 2009/0309835 A1 Dec. 17, 2009

(51) Int. Cl.
*B01D 61/32* (2006.01)
*G06F 15/16* (2006.01)

(52) U.S. Cl. ............. 210/646; 210/143; 210/321.6; 210/739; 210/138; 345/173; 604/5.01; 700/273; 709/213; 709/215; 709/230; 709/246

(58) Field of Classification Search ............ 210/143, 210/321.6, 321.71, 645, 646, 739, 138; 604/5.01, 604/6.09; 345/173; 700/2–5, 173; 709/208, 709/209, 213–216, 227, 230, 246, 220; 715/700, 715/733; 705/2
See application file for complete search history.

(56) References Cited

U.S. PATENT DOCUMENTS

| | | | |
|---|---|---|---|
| 4,370,983 A * | 2/1983 | Lichtenstein | 600/301 |
| 5,324,422 A | 6/1994 | Colleran et al. | |
| 5,421,823 A | 6/1995 | Kamen et al. | |
| 5,431,626 A | 7/1995 | Bryant et al. | |
| 5,438,510 A | 8/1995 | Bryant et al. | |
| 5,472,614 A * | 12/1995 | Rossi | 210/646 |
| 5,492,125 A | 2/1996 | Kim et al. | |
| 5,609,770 A * | 3/1997 | Zimmerman et al. | 210/739 |
| 5,618,441 A * | 4/1997 | Rosa et al. | 210/739 |
| 5,788,851 A | 8/1998 | Kenley et al. | |
| 5,903,211 A | 5/1999 | Flego et al. | |
| 6,016,396 A * | 1/2000 | Mochizuki | 717/149 |
| 6,146,523 A * | 11/2000 | Kenley et al. | 210/143 |
| 6,503,062 B1 | 1/2003 | Gray et al. | |
| 6,808,369 B2 | 10/2004 | Gray et al. | |
| 6,814,547 B2 | 11/2004 | Childers et al. | |
| 6,842,795 B2 * | 1/2005 | Keller | 710/15 |
| 6,868,309 B1 * | 3/2005 | Begelman | 700/273 |
| 6,929,751 B2 | 8/2005 | Bowman, Jr. et al. | |
| 7,082,106 B2 | 7/2006 | Sharma et al. | |
| 7,083,719 B2 | 8/2006 | Bowman, Jr. et al. | |
| 7,922,899 B2 * | 4/2011 | Vasta et al. | 210/143 |
| 2007/0156457 A1 | 7/2007 | Brown | |
| 2007/0216700 A1 | 9/2007 | Chen et al. | |
| 2008/0040151 A1 * | 2/2008 | Moore | 705/2 |

FOREIGN PATENT DOCUMENTS

WO  WO 2006/131775 A1  12/2006
WO  WO 2007/053683 A2  5/2007

OTHER PUBLICATIONS

Newton IQ Cycler Operator Manual, Part No. 470203 Rev. F, 2000-2006.

Heitmeier et al., "Sicherheitstechnik bei einem mikroprozessorgesteuerten Hämodialysegerät", Medizintechnik, 105. Jg, pp. 118-124, translation provided.

* cited by examiner

*Primary Examiner* — Joseph Drodge

(74) *Attorney, Agent, or Firm* — Fish & Richardson P.C.

(57) ABSTRACT

This patent application relates generally to processing devices in the medical device area.

51 Claims, 7 Drawing Sheets

USER INTERFACE PROCESSING DEVICE

TECHNICAL FIELD

This patent application relates generally to processing devices in the medical device area.

BACKGROUND

Hemodialysis is a process which employs a machine that includes a dialyzer to aid patients whose renal function has deteriorated to the point where their body cannot adequately rid itself of toxins.

SUMMARY

In general, in some aspects, a method for sharing one or more user interface devices between a first processing device and a second processing device is performed by one or more user interface processing devices. A dialysis device includes the one or more user interface processing devices, the first processing device, and the second processing device. The method includes switching focus from the first processing device to the second processing device or from the second processing device to the first processing device. The first processing device is configured to monitor dialysis functions of the dialysis device. The method also includes, when the first processing device has focus, managing first communications between the one or more user interface devices and the first processing device and permitting the one or more user interface devices to affect operation of the first processing device. The method also includes, when the second processing device has focus, managing second communications between the one or more user interface devices and the second processing device and permitting the one or more user interface devices to affect operation of the second processing device.

Implementations may include one or more of the following features.

The dialysis device may also include the one or more user interface devices. The method may also include switching focus from the second processing device to the first processing device responsively to a request. The method may also include receiving the request from the first processing device. The request may be based on monitoring of the dialysis device by the first processing device. The request may be responsive to a dialysis device alarm. The request may be indicative of at least one of a first condition of the dialysis device or a second condition of a patient receiving treatment from the dialysis device.

In the method, switching focus may include switching focus from the first processing device to the second processing device or from the second processing device to the first processing device responsively to a switch command received from one user interface device of the one or more user interface devices. The one user interface device may include a keyboard. The switch command may include at least one of a press code or a release code. The press code or the release code may correspond to a key on the keyboard.

In the method, managing second communications between the one or more user interface devices and the second processing device may include translating first codes received from the one or more user interface devices into second codes. Managing second communications may also include sending the second codes to the second processing device. Managing second communications may also include switching focus from the second processing device to the first processing device if no first codes are received from the one or more user interface devices for a first period of time.

In the method, the second processing device may include a microprocessor embedded within the dialysis device. The first processing device may include the one or more user interface processing devices The method may also include sending first and second protocol data to the first and second processing devices, respectively, so that the first and second processing devices are configured to maintain one or more respective connections with the one or more user interface devices, irrespective of which processing device of the first and second processing devices has focus.

In the method, the one or more user interface devices may include a keyboard. The method may also include interpreting one or more codes as a switch command. The method may also include, responsively to the switch command, switching focus from the first processing device to the second processing device or from the second processing device to the first processing device. The keyboard may include a key, and the keyboard may be configured to send the one or more codes to the one or more user interface processing devices when the key is pressed.

In the method, the one or more user interface devices may include a pointing device. The pointing device may include at least one of a mouse, a trackball, or a touchpad. The one or more user interface devices may include a display. The display may include a touch screen.

The method may also include isolating the second processing device from the first processing device so that if the second processing device experiences a condition, the first processing device and the dialysis functions of the dialysis device are not affected by the condition. The condition may include at least one of a shut down of the second processing device or a computer virus. The method may also include restarting the second processing device without affecting the first processing device and the dialysis functions of the dialysis device.

In the method, managing second communications between the one or more user interface devices and the second processing device may include translating first codes received from the one or more user interface devices into second codes. The second codes may be of one or more respective formats. The one or more respective formats may be compatible with the second processing device. Managing second communications may also include sending the second codes to the second processing device.

In the method, managing first communications between the one or more user interface devices and the first processing device may include translating first codes received from the one or more user interface devices into second codes. The second codes may be of one or more respective formats. The one or more respective formats may be compatible with the first processing device. Managing first communications may also include sending the second codes to the first processing device.

The method may also include, prior to switching focus from the first processing device to the second processing device, translating first codes received from the one or more user interface devices into second codes. The second codes may be of one or more respective first formats. The one or more respective first formats may be compatible with the first processing device. The method may also include, prior to switching focus from the first processing device to the second processing device, sending the second codes to the first processing device. The method may also include, after switching focus from the first processing device to the second processing device, stopping sending the second codes to the first processing device, temporarily ignoring any codes received from the one or more user interface devices, and translating third codes received from the one or more user interface devices into fourth codes. The fourth codes may be of one or more respective second formats. The one or more respective second formats may be compatible with the second processing device. The method may also include, after switching focus from the first processing device to the second processing device, sending the fourth codes to the second processing device. The method may also include, after switching focus from the first processing device to the second processing device, saving first configuration data. The first configuration data may be related to the one or more user interface devices and the first processing device. The method may also include, after switching focus from the first processing device to the second processing device, retrieving second configuration data. The second configuration data may be related to the one or more user interface devices and the second processing device. The method may also include, after switching focus from the first processing device to the second processing device, configuring the one or more user interface devices using the second configuration data. In the method, the one or more user interface devices may include a keyboard. The keyboard may include a key. The first and third codes may include press codes and release codes. The first configuration data may include a first state of the key. The first state may be prior to switching focus from the first processing device to the second processing device. The second configuration data may include second state of the key. The second state may be from a previous period in which the second processing device had focus. The previous period may be prior to a present period in which the second processing device has focus. In the method, the one or more user interface devices may include a pointing device. The pointing device may include one or more keys. The first and third codes may include pointing device codes. The pointing device codes may correspond to at least one of movement of the pointing device, movement of a digit along a surface of the pointing device, or press codes and release codes corresponding to the one or more keys. The point device may include a touchpad.

The method may also include, prior to switching focus from the first processing device to the second processing device, saving first configuration data. The first configuration data may be related to the one or more user interface devices and the first processing device. The method may also include, prior to switching focus from the first processing device to the second processing device, sending first codes to the first processing device. The first codes may be of one or more respective first formats. The one or more respective first formats may be related to the first configuration data. The method may also include, after switching focus from the first processing device to the second processing device, retrieving second configuration data. The second configuration data may be related to the one or more user interface devices and the second processing device. The method may also include, after switching focus from the first processing device to the second processing device, configuring the one or more user interface devices using the second configuration data, and saving the second configuration data. The method may also include, after switching focus from the first processing device to the second processing device, stopping sending the first codes to the first processing device, temporarily ignoring any codes received from the one or more user interface devices, and sending second codes to the second processing device. The second codes may be of one or more respective second formats. The one or more respective second formats may be related to the second configuration data. In the method, the one or more user interface devices may include a display and a touch screen controller. The display may include a touch screen. The first and second codes may include touch screen codes received from the touch screen controller. The first configuration data may include a first configuration state of the touch screen controller corresponding to the first processing device. The first configuration state may be prior to switching focus from the first processing device to the second processing device. The second configuration data may include a second configuration state of the touch screen controller corresponding to the second processing device. The second configuration state may be from a previous period in which the second processing device had focus, the previous period being prior to a present period in which the second processing device has focus. The one or more user interface processing devices may include the touch screen controller. In the method, temporarily ignoring any codes received from the one or more user interface devices may include temporarily ignoring any codes received from the touch screen controller relating to interactions of a user with the touch screen The method may also include, prior to switching focus from the second processing device to the first processing device, translating first codes received from the one or more user interface devices into second codes. The second codes may be of one or more respective second formats. The one or more respective second formats may be compatible with the second processing device. The method may also include, prior to switching focus from the second processing device to the first processing device, sending the second codes to the second processing device. The method may also include, after switching focus from the second processing device to the first processing device, stopping sending the second codes to the second processing device, temporarily ignoring any codes received from the one or more user interface devices, and translating third codes received from the one or more user interface devices into fourth codes. The fourth codes may be of one or more respective first formats. The one or more respective first formats may be compatible with the first processing device. The method may also include, after switching focus from the second processing device to the first processing device, sending the fourth codes to the first processing device. The method may also include, after switching focus from the second processing device to the first processing device, saving second configuration data. The second configuration data being may be related to the one or more user interface devices and the second processing device. The method may also include, after switching focus from the second processing device to the first processing device, retrieving first configuration data. The first configuration data may be related to the one or more user interface devices and the first processing device. The method may also include, after switching focus from the second processing device to the first processing device, configuring the one or more user interface devices using the first configuration data.

The method may also include, prior to switching focus from the second processing device to the first processing device, saving second configuration data. The second configuration data may be related to the one or more user interface devices and the second processing device.

The method may also include, prior to switching focus from the second processing device to the first processing device, sending second codes to the second processing device. The second codes may be of one or more respective second formats. The one or more respective second formats may be related to the second configuration data. The method may also include, after switching focus from the second processing device to the first processing device, retrieving first configuration data. The first configuration data may be related to the one or more user interface devices and the first processing device. The method may also include, after switching focus from the second processing device to the first processing device, configuring the one or more user interface devices using the first configuration data, and saving the first configuration data. The method may also include, after switching focus from the second processing device to the first processing device, stopping sending the second codes to the second processing device, temporarily ignoring any codes received from the one or more user interface devices, and sending first codes to the first processing device. The first codes may be of one or more respective first formats. The one or more respective first formats may be related to the first configuration data.

The method may also include, after switching focus from the second processing device to the first processing device, sending a mute command to an audio device. The dialysis device may further include the audio device. When the second processing device has focus, the second processing device may be configured to control the audio device.

In some aspects, a dialysis device includes one or more user interface devices, means for monitoring dialysis functions of the dialysis device, and means for performing non-dialysis functions. The non-dialysis functions include data entry functions. The dialysis device also includes means for switching focus from the monitoring means to the performing means or from the performing means to the monitoring means. The dialysis device also includes means for, when the means for monitoring has focus, managing first communications between the one or more user interface devices and the means for monitoring and for permitting the one or more user interface devices to affect operation of the means for monitoring. The dialysis device also includes means for, when the means for performing has focus, managing second communications between the one or more user interface devices and the means for performing and permitting the one or more user interface devices to affect operation of the means for performing.

In some aspects, one or more machine-readable media store instructions that are executable to share one or more user interface devices between a first processing device and a second processing device. A dialysis device includes one or more user interface processing devices, the first processing device, and the second processing device. The instructions are for causing the one or more user interface processing devices to switch focus from the first processing device to the second processing device or from the second processing device to the first processing device. The first processing device is configured to monitor dialysis functions of the dialysis device. The instructions are also for causing the one or more user interface processing devices to, when the first processing device has focus, manage first communications between the one or more user interface devices and the first processing device and permit the one or more user interface devices to affect operation of the first processing device. The instructions are also for causing the one or more user interface processing devices to, when the second processing device has focus, manage second communications between the one or more user interface devices and the second processing device and permit the one or more user interface devices to affect operation of the second processing device.

Implementations may include one or more of the following features.

In the one or more machine-readable media, the instructions may further include instructions for causing the one or more user interface processing devices to switch focus from the second processing device to the first processing device responsively to a request. The request may be responsive to a dialysis device alarm.

In the one or more machine-readable media, the instructions may further include instructions for causing the one or more user interface processing devices to isolate the second processing device from the first processing device so that if the second processing device experiences a condition, the first processing device and the dialysis functions of the dialysis device are not affected by the condition.

In the one or more machine-readable media, the instructions may further include instructions for causing the one or more user interface processing devices to, prior to switching focus from the first processing device to the second processing device, translate first codes received from the one or more user interface devices into second codes. The second codes may be of one or more respective first formats. The one or more respective first formats may be compatible with the first processing device. The instructions may further include instructions for causing the one or more user interface processing devices to, prior to switching focus from the first processing device to the second processing device, send the second codes to the first processing device. The instructions may further include instructions for causing the one or more user interface processing devices to, after switching focus from the first processing device to the second processing device, stop sending the second codes to the first processing device, temporarily ignore any codes received from the one or more user interface devices, and translate third codes received from the one or more user interface devices into fourth codes. The fourth codes may be of one or more respective second formats. The one or more respective second formats may be compatible with the second processing device. The instructions may further include instructions for causing the one or more user interface processing devices to, after switching focus from the first processing device to the second processing device, send the fourth codes to the second processing device.

In the one or more machine-readable media, the instructions may further include instructions for causing the one or more user interface processing devices to, prior to switching focus from the first processing device to the second processing device, save first configuration data. The first configuration data may be related to the one or more user interface devices and the first processing device. In the one or more machine-readable media, the instructions may further include instructions for causing the one or more user interface processing devices to, prior to switching focus from the first processing device to the second processing device, send first codes to the first processing device. The first codes may be of one or more respective first formats. The one or more respective first formats may be related to the first configuration data. The instructions may further include instructions for causing the one or more user interface processing devices to, after switching focus from the first processing device to the second processing device, retrieve second configuration data. The second configuration data may be related to the one or more user interface devices and the second processing device. The instructions may further include instructions for causing the one or more user interface processing devices to, after switching focus from the first processing device to the second processing device, configure the one or more user interface devices using the second configuration data, and save the second configuration data. The instructions may further include instructions for causing the one or more user interface processing devices to, after switching focus from the first processing device to the second processing device, stop sending the first codes to the first processing device, temporarily ignore any codes received from the one or more user interface devices, and send second codes to the second processing device. The second codes may be of one or more respective second formats. The one or more respective second formats may be related to the second configuration data.

In some aspects, a dialysis device is configured to share one or more user interface devices between a first processing device and a second processing device. The dialysis device includes the first processing device, the second processing device, memory configured to store instructions for execution, and one or more user interface processing devices configured to execute the instructions. The instructions are for causing the one or more user interface processing devices to switch focus from the first processing device to the second processing device or from the second processing device to the first processing device. The first processing device is configured to monitor dialysis functions of the dialysis device. The instructions are for causing the one or more user interface processing devices to, when the first processing device has focus, manage first communications between the one or more user interface devices and the first processing device and permit the one or more user interface devices to affect operation of the first processing device. The instructions are for causing the one or more user interface processing devices to, when the second processing device has focus, manage second communications between the one or more user interface devices and the second processing device and permit the one or more user interface devices to affect operation of the second processing device.

Implementations may include one or more of the following features.

The dialysis device may also include the one or more user interface devices. In the dialysis device, the instructions may also include instructions for causing the one or more user interface processing devices to switch focus from the second processing device to the first processing device responsively to a request. The request may be responsive to a dialysis device alarm.

In the dialysis device, the instructions may also include instructions for causing the one or more user interface processing devices to isolate the second processing device from the first processing device so that if the second processing device experiences a condition, the first processing device and the dialysis functions of the dialysis device are not affected by the condition.

In the dialysis device, the instructions may also include instructions for causing the one or more user interface processing devices to, prior to switching focus from the first processing device to the second processing device, translate first codes received from the one or more user interface devices into second codes. The second codes may be of one or more respective first formats. The one or more respective first formats may be compatible with the first processing device. The instructions may also include instructions for causing the one or more user interface processing devices to, prior to switching focus from the first processing device to the second processing device, send the second codes to the first processing device. The instructions may also include instructions for causing the one or more user interface processing devices to, after switching focus from the first processing device to the second processing device, stop sending the second codes to the first processing device, temporarily ignore any codes received from the one or more user interface devices, and translate third codes received from the one or more user interface devices into fourth codes. The fourth codes may be of one or more respective second formats. The one or more respective second formats may be compatible with the second processing device. The instructions may also include instructions for causing the one or more user interface processing devices to, after switching focus from the first processing device to the second processing device, send the fourth codes to the second processing device.

In the dialysis device, the instructions may also include instructions for causing the one or more user interface processing devices to, prior to switching focus from the first processing device to the second processing device, save first configuration data. The first configuration data may be related to the one or more user interface devices and the first processing device. The instructions may also include instructions for causing the one or more user interface processing devices to, prior to switching focus from the first processing device to the second processing device, send first codes to the first processing device. The first codes may be of one or more respective first formats. The one or more respective first formats may be related to the first configuration data. The instructions may also include instructions for causing the one or more user interface processing devices to, after switching focus from the first processing device to the second processing device, retrieve second configuration data. The second configuration data may be related to the one or more user interface devices and the second processing device. The instructions may also include instructions for causing the one or more user interface processing devices to, after switching focus from the first processing device to the second processing device, configure the one or more user interface devices using the second configuration data, and save the second configuration data. The instructions may also include instructions for causing the one or more user interface processing devices to, after switching focus from the first processing device to the second processing device, stop sending the first codes to the first processing device, temporarily ignore any codes received from the one or more user interface devices, and send second codes to the second processing device. The second codes may be of one or more respective second formats. The one or more respective second formats may be related to the second configuration data.

In some aspects, a method for sharing one or more user interface devices between a first processing device and a second processing device is performed by one or more user interface processing devices. A dialysis device includes the one or more user interface processing devices, the first processing device, and the second processing device. The method includes, in a first mode, permitting the one or more user interface devices to affect operation of the first processing device. The method also includes, in a second mode, permitting the one or more user interface devices to affect operation of the second processing device. The method also includes switching from the first mode to the second mode in response to a first command from one user interface device of the one or more user interface devices. The method also includes switching from the second mode to the first mode in response to at least one of a second command from the one user interface device, or a request received from the first processing device. The first processing device is configured to monitor dialysis functions of the dialysis device.

In some aspects, one or more machine-readable media store instructions that are executable to share one or more user interface devices between a first processing device and a second processing device. A dialysis device includes one or more user interface processing devices, the first processing device, and the second processing device. The instructions are for causing the one or more user interface processing devices to, in a first mode, permit the one or more user interface devices to affect operation of the first processing device. The instructions are also for causing the one or more user interface processing devices to, in a second mode, permit the one or more user interface devices to affect operation of the second processing device. The instructions are also for causing the one or more user interface processing devices to switch from the first mode to the second mode in response to a first command from one user interface device of the one or more interface devices. The instructions are also for causing the one or more user interface processing devices to switch from the second mode to the first mode in response to at least one of a second command from the user interface device, or a request received from the first processing device. The first processing device is configured to monitor dialysis functions of the dialysis device.

In some aspects, a dialysis device is configured to share one or more user interface devices between a first processing device and a second processing device. The dialysis device includes the first processing device, the second processing device, memory configured to store instructions for execution, and one or more user interface processing devices configured to execute the instructions. The instructions are for causing the one or more user interface processing devices to, in a first mode, permit the one or more user interface devices to affect operation of the first processing device. The instructions are also for causing the one or more user interface processing devices to, in a second mode, permit the one or more user interface devices to affect operation of the second processing device. The instructions are also for causing the one or more user interface processing devices to switch from the first mode to the second mode in response to a first command from one user interface device of the one or more user interface devices. The instructions are also for causing the one or more user interface processing devices to switch from the second mode to the first mode in response to at least one of a second command from the user interface device, or a request received from the first processing device. The first processing device is configured to monitor dialysis functions of the dialysis device.

The foregoing methods may be implemented as one or more machine-readable media storing instructions that are executable on one or more processing device to implement the methods. The foregoing methods may be implemented as a computer program product comprised of instructions that are stored on one or more machine-readable media, and that are executable on one or more processing devices. The foregoing methods may be implemented as an apparatus or system that includes one or more processing devices and memory to store executable instructions to implement the methods.

The details of one or more examples are set forth in the accompanying drawings and the description below. Further features, aspects, and advantages will become apparent from the description, the drawings, and the claims.

DETAILED DESCRIPTION

Figure 1:
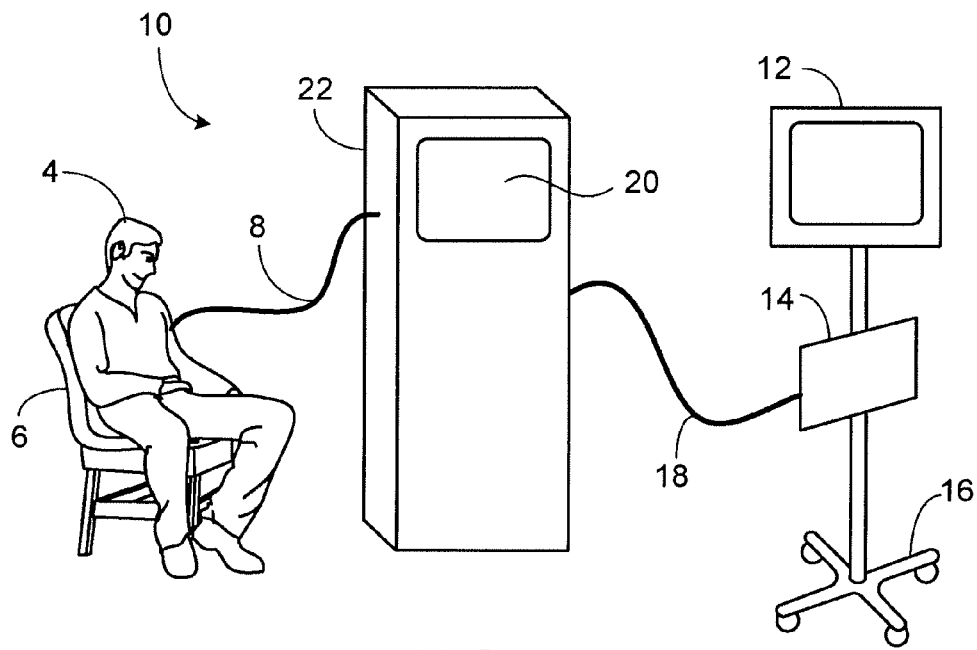
FIG. 1 is diagram showing an example of a patient care environment.

Hemodialysis is a process which employs a machine that includes a dialyzer to aid patients whose renal function has deteriorated to the point where their body cannot adequately rid itself of toxins. The dialyzer includes a semi-permeable membrane, the membrane serving to divide the dialyzer into two chambers. Blood is pumped through one chamber and a dialysis solution through the second. As the blood flows by the dialysis fluid, impurities, such as urea and creatinine, diffuse through the semi-permeable membrane into the dialysis solution. The electrolyte concentration of the dialysis fluid is set so as to maintain electrolytic balance within the patient.

Further purification in a dialyzer is possible through ultrafiltration. Ultrafiltration results from the normal situation wherein there is a positive pressure differential between the blood and the dialysis fluid chambers. This pressure differential causes water in the blood to pass through the membrane into the dialysis solution. This provides the benefit of reducing a dialysis patient's excess water load which normally would be eliminated through proper kidney functioning.

Patients undergoing dialysis therapy typically travel three or more times per week to hospital or dialysis centers that are designed for efficient and routine dialysis therapy. Hemodialysis is a complex treatment process in which, typically, an arterio-venous shunt, frequently termed a "fistula," is surgically inserted between a patient's artery and vein to facilitate transfer of blood from the patient to the dialyzer. During a normal dialysis treatment, one end of an arterial line or tube is inserted into the upstream end of the fistula (i.e., at a point near the patient's artery) and transports blood withdrawn from the upstream portion of the fistula to the inlet of the dialyzer; a venous line or tube connected to the output of the blood side of the dialyzer returns treated blood to the fistula at an insertion point downstream of the arterial line (i.e., at a point near the patient's vein).

Since dialysis involves removing blood from and returning blood to a patient, performing a dialysis procedure carries a degree of risk. Successful dialysis treatment requires monitoring of several patient vital signs and hemodialysis parameters during the dialysis process in order to optimize the overall efficacy of the dialysis procedure, to assess the condition of the fistula (the access to the patient's blood) and to determine the actual purification achieved. Some examples of parameters monitored and analyzed by a hemodialysis machine or equipment include the blood access flow rate or the rate at which blood flows out of the patient to the dialyzer, a critical parameter; and the ratio Kt/V to measure dialysis efficiency, where K is the clearance or dialysance (both terms representing the purification efficiency of the dialyzer), t is treatment time and V is the patient's total water value.

A processing device located on the hemodialysis machine may be used to manage and oversee the functions of the hemodialysis process and to, for example, monitor, analyze and interpret patient vital signs and hemodialysis parameters during a hemodialysis procedure. A health care practitioner such as a nurse, a patient care technician (or a home health aide if dialysis is performed at a patient's home) may oversee the dialysis treatment sessions. Data provided by the hemodialysis machine and the processing device may aid the health care practitioner in performing his or her duties.

Health care practitioners are often tasked with duties other than dialysis treatment oversight. For example, dialysis treatment centers must manage a large amount of data that must be entered and recorded. In addition to patient blood pressure, pulse, and select treatment parameters, other data relating to the patient may be entered, tracked, and coordinated, such as patient identity information, scheduling information, and billing information. Computing devices have been utilized to assist with data entry.

FIG. 1 shows an example of a patient care environment 10 in which a patient 4 seated in a chair 6 receives medical treatment from a treatment station 22. The medical treatment is, for example, dialysis, and, more particularly, hemodialysis. The treatment station 22 may be a hemodialysis treatment station or hemodialysis device. A tube or arterial line 8 transports blood from the patient 4 to the hemodialysis device 22 and back again to the patient 4 after processing and treatment in the hemodialysis device 22. The hemodialysis device 22 with display 20 is connected via cabling 18 to a processor 14 which controls a touch screen display 12. The touch screen display 12 is mounted on a movable stand 16. The touch screen display 12 includes a touch screen that permits a health care practitioner (HCP) such as a nurse, a patient care technician (or a home health aide if dialysis is performed at a patient's home), or even a patient to press the display 12 to, for example, enter patient or other data.

Figure 2:
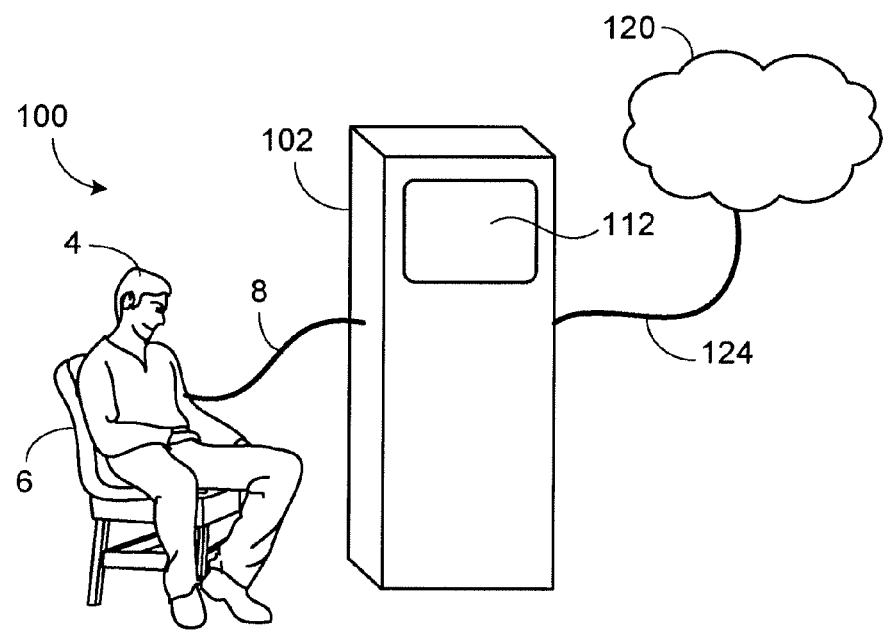
FIG. 2 is a diagram showing another example of a patient care environment.

FIG. 2 is a diagram of a patient care environment 100 in which the patient 4 is seated in the chair 6 and receives medical treatment from a treatment station 102. The treatment station 102 may be any medical device, for example, a dialysis device. Most particularly, the treatment station 102 may be a hemodialysis treatment station or hemodialysis device. The tube or arterial line 8 is, once again, used for transporting blood from the patient 4 to the hemodialysis (HD) device 102 and back again to the patient 4 after processing and treatment of the blood in the HD device 102. The HD device 102 may be configured to communicate with an external network 120, such as a local-area network or the Internet, via a wired or wireless connection 124.

The HD device 102 may include a display 112 with, e.g., touch screen features. The HD device 102 may centralize and consolidate hemodialysis functions and data entry functions in a single device 102, without, e.g., the use of a separate, external display (e.g., display 12 of FIG. 1) or a separate, external processor (e.g., processor 14) with associated equipment (e.g., movable stand 16). Consolidation of functions in a single HD device 102 may also reduce the amount of external cabling (e.g., cabling 18) to the device 102. The HD device 102 may reduce the amount of space needed for hemodialysis treatment and present less crowding of the patient care environment 100. An HCP may be able to focus solely on the HD device 102, or the display 112 of the HD device 102, without the HCP's attention being diverted to, e.g., another external display. The HD device 102 may reduce power consumption and cost as compared to other, non-centralized implementations.

Due to the complex and precise nature of the hemodialysis process, hemodialysis functions are, in general, far more critical to the safety and well-being of the patent 4 connected to the HD device 102 than other functions, such as patient data entry, that may be performed using the device 102. In the event that functions other than hemodialysis functions are to be integrated into the HD device 102, isolation of these functions from the hemodialysis functions may be achieved through the use of more than one processing device.

Use of more than one processing device may present its own set of design challenges since different processing devices used for different functions may be incompatible with one another and may communicate with, e.g., user interface devices (not shown in FIG. 2) in different, incompatible ways.

Figure 3:
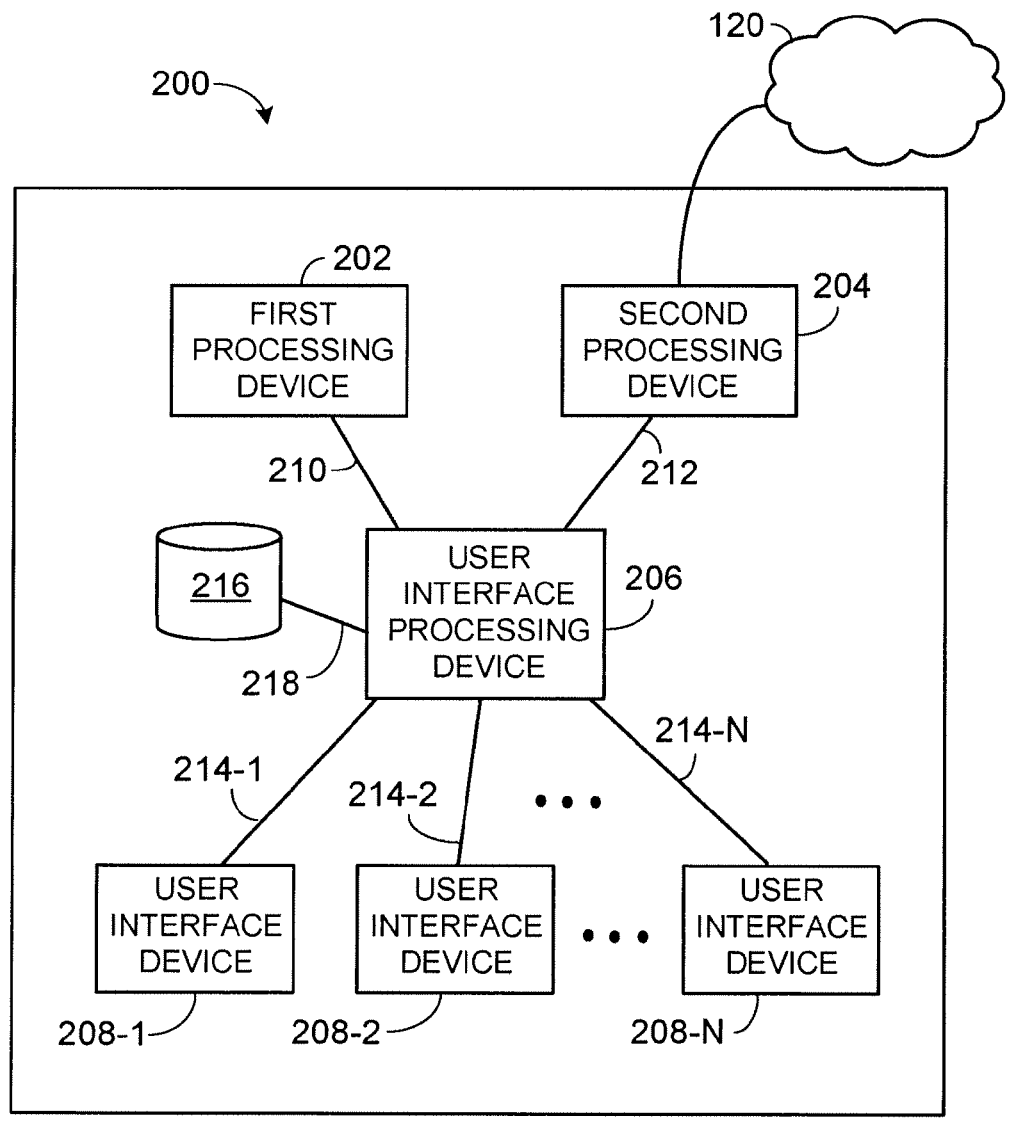
FIG. 3 is a block diagram of an example hemodialysis machine.

FIG. 3 is a block diagram of an example implementation 200 of the HD device 102. A user interface processing device (UIP) 206 is configured to share user interface resources, i.e., user interface devices 208-1, 208-2, . . . , 208-N, between a first processing device 202 and a second processing device 204. Both the first and the second processing devices 202, 204 are connected to the UIP 206 via respective connections 210, 212, while the user interface devices 208-1, 208-2, . . . , 208-N are connected to the UIP 206 via connections 214-1, 214-2, . . . , 214-N. Although one UIP 206 is shown in FIG. 3, several user interface processing devices may be used to implement the functionality of the UIP 206. The UIP 206 is connected to memory 216 via a connection 218. Other memory (not shown) may be connected to, and, used by, e.g., the first processing device 202 and/or the second processing device 204.

The user interface devices 208-1, 208-2, . . . , 208-N may include any of a variety of user interface devices known in the art, such as an alphanumeric keyboard or a keypad, a pointing device (e.g., a touchpad, a mouse, or a trackball), a display, and a display with a touch screen. In an implementation, one or more of the user interface devices 208-1, 208-2, . . . , 208-N may be located external to the HD device 200.

The second processing device 204 of the HD device 200 may be configured to communicate with the external network 120, such as a local-area network or the Internet, via a wired or wireless connection 124 (and, e.g., via a network interface (not shown)). In other implementations, other processing devices such as the UIP 206 or the first processing device 202 may communicate with an external network such as the external network 120.

As described above, the UIP 206 is configured to share the user interface devices 208-1, 208-2, . . . , 208-N between the first processing device 202 and the second processing device 204. The UIP 206 may switch focus from the first processing device 202 to the second processing device 204. The UIP 206 may likewise switch focus from the second processing device 204 to the first processing device 202.

A processing device, such as the first or the second processing device 202, 204 of FIG. 3, may be said to have focus. For example, a processing device has focus when the processing device has control of, and/or is controlled by, one or more user interface devices connected to, or communicating with, the processing device (e.g., via one or more user interface processing devices). That is, in this example, when a processing device has focus, a user interface device (such as a keyboard) connected to, or communicating with, the processing device (e.g., via one or more user interface processing devices) will generally affect operation of the processing device. User interactions with a user interface device will likewise generally affect operation of the processing device in this instance. Likewise, in this example, when a processing device has focus, the processing device may control a user interface device (such as a video display) connected to, or communicating with, the processing device (e.g., via one or more user interface processing devices).

When a processing device, such as the first or the second processing device 202, 204 of FIG. 3, does not have focus, then, for example, the processing device may not have control of and/or be controlled by one or more user interface devices connected to, or communicating with, the processing device (e.g., via one or more user interface processing devices). Rather, another processing device may have been given focus. One or more user interface processing devices such as the UIP 206 may send protocol data to the processing device, even when the processing device does not presently have focus, so that the processing device may be configured to maintain connections with one or more user interface devices. That is, from the perspective of the processing device, even when the processing device does not have focus, the processing device may have a connection maintained with a user interface device that the processing device does not control and/or that is not controlled by the processing device when the processing device does not have focus. The UIP 206 may therefore send protocol data related to the one or more user interface devices to the first and the second processing devices 202, 204, irrespective of which processing device 202, 204 has focus.

When a processing device (such as the first processing device 202 or the second processing device 204) has focus, one or more user interface processing devices (such as the UIP 206) may manage communications between one or more user interface devices (such as the user interface devices 208-1, 208-2, . . . , 208-N) and the processing device. The UIP 206 may, when the processing device has focus, permit the user interface devices 208-1, 208-2, . . . , 208-N to affect operation of the processing device. The UIP 206 may switch between modes. The modes may be exclusive of one another and may include a mode in which the first processing device 202 has focus, and a mode in which a second processing device 204 has focus.

Figure 4:
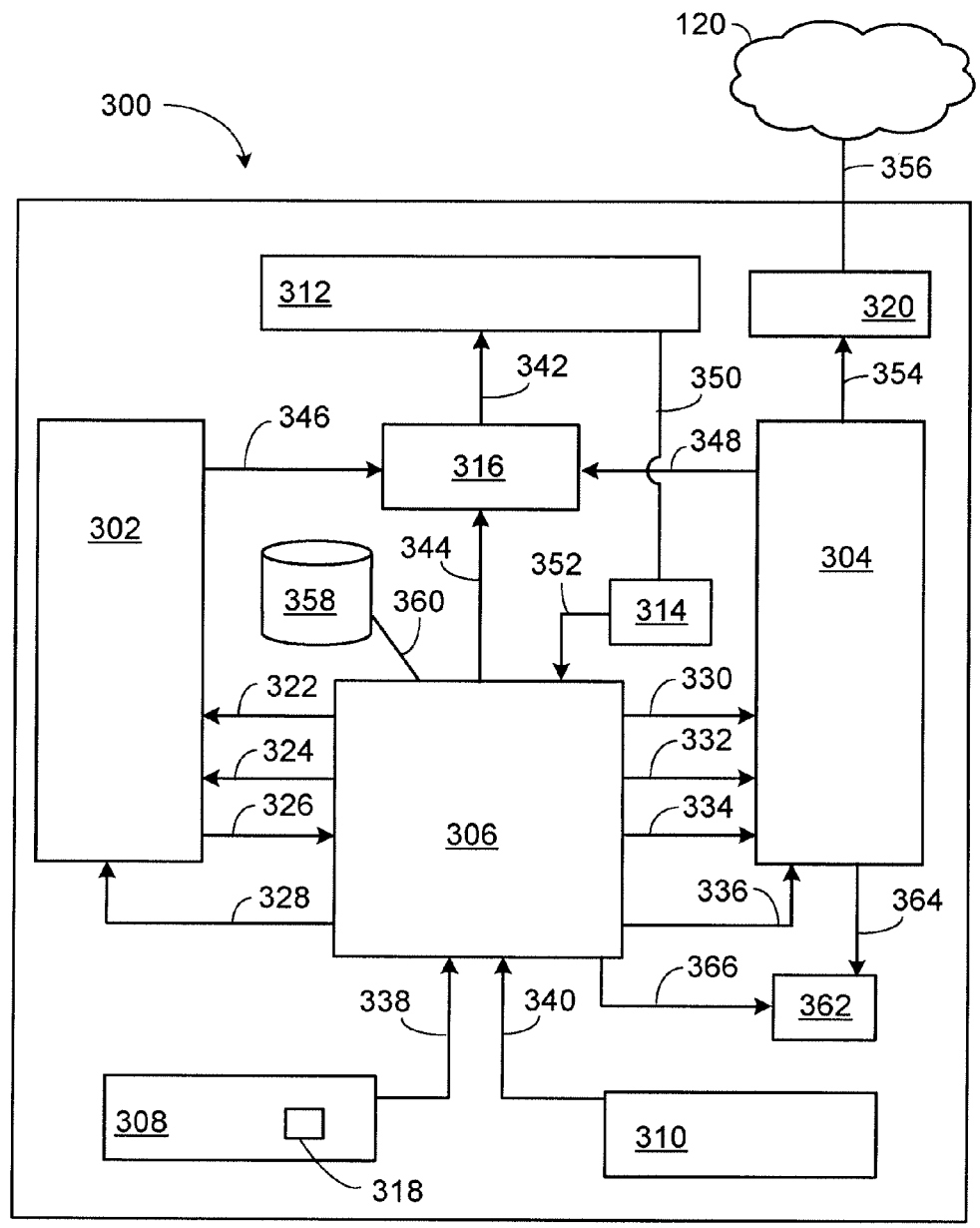
FIG. 4 is a block diagram of an example hemodialysis machine.

FIG. 4 is a block diagram of an example implementation 300 of the HD device 102. A UIP 306 is configured to share user interface resources, e.g., a keyboard 308, a pointing device 310 (such as a touchpad), and a display 312 with a touch screen, between a first processing device 302 and a second processing device 304. The first processing device 302 may be a functional hemodialysis processing device (FHP) 302 that may be configured to monitor hemodialysis functions of the HD device 300. The second processing device 304 may be a microprocessor, such as a standard personal computer (PC) processor, embedded within the HD device 300, and may be referred to as an embedded processing device (EP) 304. The FHP 302 is connected to the UIP 306 via connections 322, 324, 326, 328, and the EP 304 is connected to the UIP 306 via connections 330, 332, 334, 336. The keyboard 308 is connected to the UIP 306 via connection 338. The pointing device 310 is connected to the UIP 306 via connection 340. The display 312 is connected to a digital video switch 316 via connection 342, which is in turn connected to the UIP 306, the FHP 302, and the EP 304 via respective connections 344, 346, 348. A touch screen controller 314 is connected to the display 312 via connection 350, and to the UIP 306 via connection 352. Although one UIP 306 is shown in FIG. 4, several user interface processing devices may be used to implement the functionality of the UIP 306. The UIP 306 is connected to memory 358 via a connection 360. Other memory (not shown) may be connected to, and, used by, e.g., the FHP 302 and/or the EP 304. The EP 304, for example, may utilize a flash memory rather than a conventional hard drive. The HD device 300 also includes an audio device 362. The audio device 362 is connected to the EP 304 via connection 364 and the UIP 306 via connection 366. FIG. 4 is intended to show functional connections between devices of the HD device 300, so more or fewer connections may be used than are shown in FIG. 4.

As described above, the UIP 306 may switch focus from the FHP 302 to the EP 304. The UIP 306 may likewise switch focus from the EP 304 to the FHP 302. When the FHP 302 has focus, the keyboard 308, the pointing device 310, and the display 312 with a touch screen (all connected to the FHP 302 via the UIP 306) will generally affect operation of the FHP 302. When the EP 304 has focus, the keyboard 308, the pointing device 310, and the display 312 with a touch screen (all connected to the EP 304 via the UIP 306) will generally affect operation of the EP 304. User interactions with the devices 308, 310, 312 will likewise generally affect operation of whichever processing device (the FHP 302 or the EP 304) has focus. The processing device that has focus (the FHP 302 or the EP 304) may control, e.g., the display 312 in certain circumstances.

In an implementation, one or more of the user interface devices (e.g., the keyboard 308, the pointing device 310, the display 312, and the audio device 362) may be located external to the HD device 300.

In this example implementation, when the EP 304 has focus, the FHP 302 does not have focus, and the FHP 302 may not have control of and/or be controlled by the devices 308, 310, 312. When the FHP 302 has focus, the EP 304 does not have focus, and the EP 304 may not have control of and/or be controlled by the devices 308, 310, 312. The UIP 306 may send protocol data relating to the devices 308, 310, 312 to the EP 304 and the FHP 302, even when one of these devices does not have focus, so that the EP 304 and the FHP 302 may maintain connections with the devices 308, 310, 312. That is, from the perspective of the processing device (EP 304 or FHP 302) that does not have focus, a connection at least appears to be maintained with the devices 308, 310, 312, even though these devices 308, 310, 312 are not controlled by, and do not control, the processing device that does not have focus. The UIP 306 may therefore send protocol data related to the devices 308, 310, 312 to the FHP 302 and the EP 304, irrespective of which processing device 302, 304 has focus.

The UIP 306 may switch between modes. The modes may be exclusive of one another and may include a mode in which the first processing device 302 has focus, and a mode in which the second processing device 304 has focus.

Figure 5:
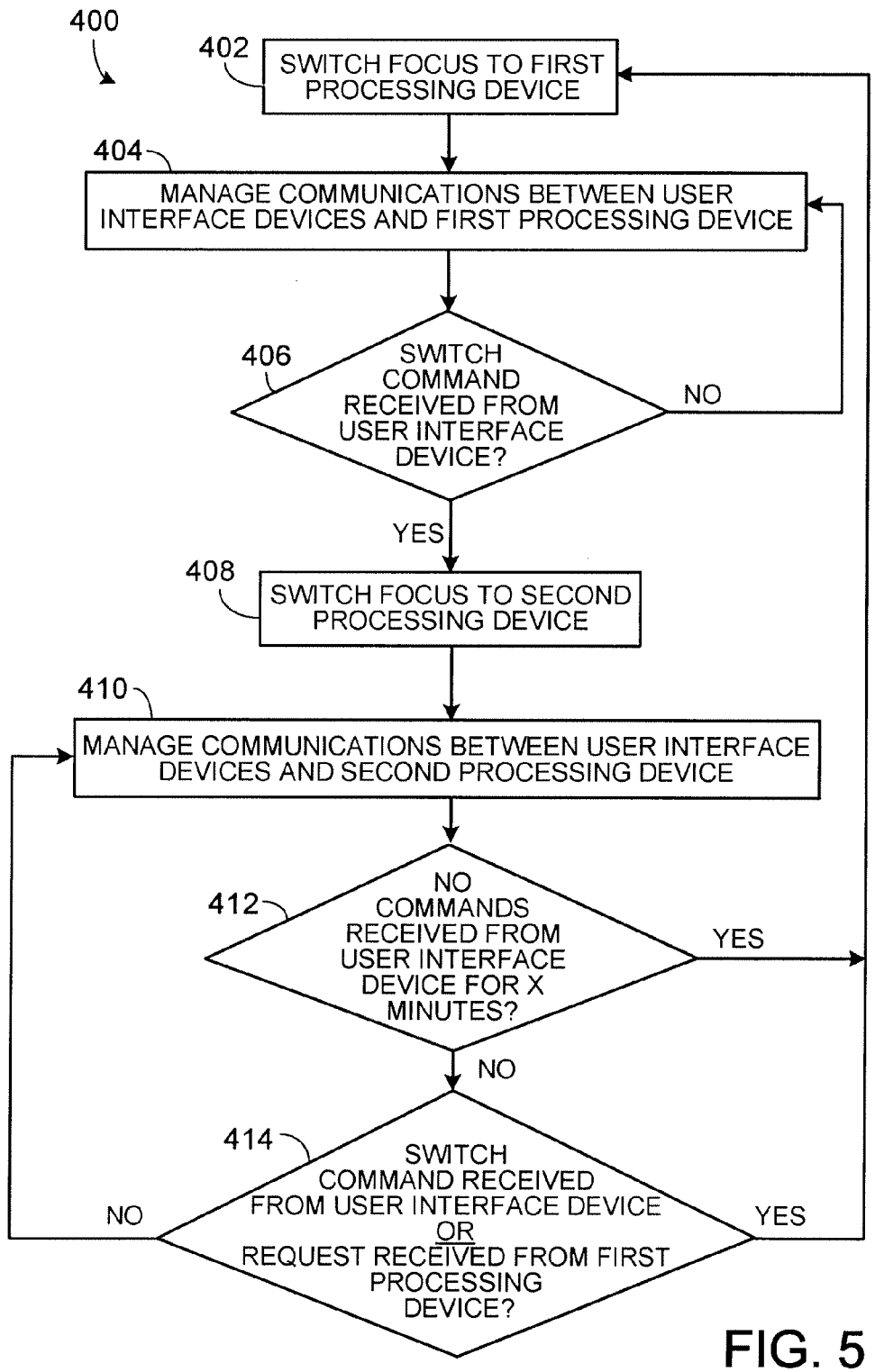
FIG. 5 is a flow diagram showing an example process of a user interface processing device.

FIG. 5 is a flow diagram showing an example process 400 of a user interface processing device such as the UIP 306. Processing begins, for example, where the UIP 306 switches (402) focus to the first processing device 302 from the second processing device 304. Thus, the FHP 302 has focus (e.g., 402, 404).

When the first processing device 302 has focus, the UIP 306 manages (404) communications between one or more user interface devices (e.g., keyboard 308, pointing device 310, and display 312 with a touch screen) and the first processing device 302. This is described in more detail below.

The UIP 306 then asks (406) whether a switch command has been received at the UIP 306 from one of the user interface devices (e.g., keyboard 308, pointing device 310, and display 312 with a touch screen). For example, the keyboard 308 may include a key 318, which, when pressed (or released) by a user causes switch command(s) in the form of key code(s) (press or release codes) to be sent to the UIP 306. A combination of keys (e.g., "CTRL-SHIFT") pressed together or in sequence, rather than a single key may also be used to trigger the switch command. The UIP 306 may be configured to interpret a particular key code or combination of key codes (simultaneous or sequential) as a switch command. The recognized key code(s) may cause the UIP 306 to switch focus from whichever processing device (here FHP 302) has focus to whichever processing device (here EP 304) does not have focus. The touch screen display 312 or the pointing device 310 may also be configured to send a switch command to the UIP 306.

If no switch command has been received at the UIP 306, focus is not switched, the FHP 302 maintains focus, and the UIP 306 continues to manage (402) communications.

If the UIP 306 has received a switch command from a user interface device such as the keyboard 308, the UIP 306 switches (408) focus to the second processing device 304 from the first processing device 302. Thus, the EP 304 has focus (e.g., 408, 410).

When the second processing device 304 has focus, the UIP 306 manages (410) communications between one or more user interface devices (e.g., keyboard 308, pointing device 310, and display 312 with a touch screen) and the second processing device 304. This is described in more detail below.

The UIP 306 then asks (412) whether any commands (e.g., codes) have been received from any of the user interface devices within the last X minutes. For this decision (412), the UIP 306 may monitor commands from less than all of the user interface devices. For example, the UIP 306 may count the time period from the last time that codes were received by the UIP 306 from the keyboard 308 but may ignore the other user interface devices for purposes of this decision (412). The time period X may be any number of minutes; for example, the time period X may be 5 minutes.

If no commands have been received from, e.g., any of the user interface devices for X minutes (a "YES" from decision 412 in FIG. 5), the UIP 306 switches (402) focus to the first processing device 302 from the second processing device 304 and processing continues as described above.

If commands have been received from, e.g., any of the user interface devices within the last X minutes (a "NO" from decision 412 in FIG. 5), the UIP 306 then asks (414) (a) whether a switch command has been received at the UIP 306 from one of the user interface devices and (b) whether a request for focus has been received from the first processing device 302.

If a switch command has been received (e.g., from the keyboard 308 as described above) OR a request for focus has been received from the first processing device 302 (due to, e.g., a condition of the HD device 300, or the patient 4 of FIG. 2, or both), the UIP 306 switches (402) focus to the first processing device 302 from the second processing device 304 and processing continues as described above.

The UIP 306 has received neither a switch command from one of the user interface devices nor a request for focus from the first processing device, If no switch command has been received at the UIP 306, focus is not switched, the EP 304 maintains focus, and the UIP 306 continues to manage (410) communications.

Referring again to FIG. 4, as mentioned above, the FHP 302 may be configured to monitor hemodialysis functions of the HD device 300. In addition to monitoring, the FHP 302 may generally control the operation of hemodialysis functions, such as operating various hemodialysis mechanical elements such as pump(s) to move blood from the patient 4 to the HD device 300 and back to the patient 4, pump(s) to place minerals into the dialysate solution in the dialyzer to enhance filtration of impurities and water from the patient's blood, pump(s) to provide water to the HD device 300, mixer(s) to mix the dialysate solution, and the like.

Some examples of hemodialysis functions and conditions that the FHP 302 may monitor include the operation of the blood pump(s), such as the blood pump rate, the patient's blood pressure on the input and the output sides of the HD device 300; the degree to which water and impurities such as urea and creatinine are filtered out of the patient's blood as it passes through the dialyzer; the conductivity and pH of the dialysate solution; the process of separating air from the patient's blood, and other functions.

The FHP 302 may be configured to generate an alarm. The alarm may be indicative of a condition of the HD device 300, such as a failure of water to be supplied to the machine, or a failure to separate air from the blood in a drip chamber of the dialyzer. The alarm may be indicative of a condition of the patient 4 who is receiving treatment from the HD device 300. For example, an alarm may be triggered in the event that the patient's blood pressure (or the blood pressure through the HD device 300) falls outside of a certain range at either the input or the output to the HD device 300. For example, the FHP 302 may detect a sudden drop in blood pressure in the HD device 300 and may generally generate an alarm. In this sense, the alarm may be indicative of both a condition of the patient 4 and a condition of the HD device 300.

The FHP 302 is connected to the UIP 306 via a connection 326, over which a control request or a request for focus may be sent from the FHP 302 to the UIP 306. When the FHP 302 sends a control request or a request for focus to the UIP 302 on the connection 326, the UIP 306, upon receipt of the request, may generally immediately switch focus from the FHP 302 (the first processing device 302) to the EP 304 (the second processing device 304) responsively to the request (e.g., 402, 414 in FIG. 5). The control request or the request for focus may generally be based on monitoring of the HD device 300 by the FHP 302 and may be indicative of, or responsive to, an alarm, which may in turn be indicative of a condition of the patient 4 or a condition of the HD device 300, or both. The request may also be indicative of either or both conditions. In this way, the control request or the request for focus provides a safety feature that allows the FHP 302 to control, or be controlled by the user interface devices (e.g., keyboard 308, pointing device 310, and display 312 with a touch screen) in the event of a patient condition or an HD device 300 condition, or both. The display 312, for example, may immediately provide an HCP with information about the hemodialysis functions of the HD device 300 and allow the HCP an interface to control the FHP 302 and thus the hemodialysis functions of the HD device 300.

The connection 326 may be a serial connection.

The FHP 302 may be a proprietary, non-standardized functional processor specifically designed and customized to control, operate and monitor hemodialysis functions of the HD device 300. For example, the FHP 302 may be a PowerPC processor with a proprietary architecture. In other implementations, the FHP 302 may be a standard personal computer (PC) compatible processor specifically programmed so that the processor controls, operates, and monitors hemodialysis functions of the HD device.

As mentioned above, the second processing device 304 may be a microprocessor, such as a standard personal computer (PC) compatible processor, embedded within the HD device 300, and may be referred to as an embedded processing device (EP) 304. The EP 304 may run a standard operating system, such as the WINDOWS® operating system from Microsoft Corporation or the LINUX® operating system.

In contrast to the first processing device 302, which controls, operates and monitors important medical functions of the HD device 300, the second processing device 304 may implement the non- or less-critical tasks on the HD device 300, such as data entry regarding the patient 4 and the patient's particular hemodialysis treatment prescription. The EP 304 may be connected to the FHP 302 via a connection (not shown in FIG. 4) such as a serial link so that the EP 304 can receive information regarding the patient's hemodialysis treatment, such as the patient's blood pressure at the input and the output of the HD device 300, the rate of the blood pump (s), the particular prescription of minerals to be used in the dialysate solution, and other like information. The hemodialysis treatment data may aid the HCP overseeing the dialysis treatment session(s) for the patient 4, and/or may be logged for future usage.

As mentioned above, HCPs are often tasked with duties other than dialysis treatment oversight. In addition to patient blood pressure, pulse, and select treatment parameters, other data relating to the patient may be entered, tracked and coordinated, such as patient identity information, scheduling information, and billing information. The second processing device 304 may generally be used for analysis of interpretation of hemodialysis treatment data as well as these other data functions and information technology tasks that are generally not critical to the operation of the HD device 300. Explanations of example patient data entry methods and devices are included in International Patent Application Publication Number WO 2007/053683 A2, published May 10, 2007, entitled "Digital Data Entry Methods and Devices", with International Application Number PCT/US2006/042650, and incorporated by reference herein. In general, the EP 304 may run any of a host of, e.g., PC compatible programs.

The EP 304 may be configured to communicate with the external network 120, such as a local-area network or the Internet, by way of a network interface 320 and via wired or wireless connections 354, 356. The network interface 320 may be a USB network connection. As such, a user of the HD device 300 may leverage the EP 304 network connection(s) for any of a variety of activities, including HCP training via the Internet, for example.

Since functions other than hemodialysis functions may generally be integrated into the HD device 300, isolation of these functions from the hemodialysis functions may be achieved through the use of more than one processing device in the HD device 300. In general, by virtue of being a separate processing device, the EP 304 does not control or affect the hemodialysis functions of the HD device 300. In addition, the UIP 306 may generally isolate the EP 304 from the FHP 302 so that if the EP 304 experiences a condition, such as a system crash, a shut down, or a computer virus, the FHP 302, and thus the hemodialysis functions of the HD device 300, are not affected by the condition. In this way, the EP 304 can succumb to the effects a computer virus or the like from the external network 120 (e.g., a public network) without impacting the critical operations of the HD device 300 or threatening patient safety. A simple system error on the EP 304 will not affect the FHP 302.

The EP 304 is connected to the UIP 306 via a connection 334, over which a reset command may be sent from the UIP 306 to the EP 304 to restart (or shut down and restart) the EP 304 in the event of a condition on the EP 304. The UIP 306 may reset the EP 304 without shutting down the FHP 302 or the HD device 300. In general, the FHP 302 and the hemodialysis functions of the HD device 300 are completely unaffected by a reset command sent from the UIP 304 to the EP 304, providing a safety feature of the HD device 300.

Although generally the UIP 306 is a separate processing device from that of the first and the second processing devices 302, 304, in an implementation, the first processing device 302 may include the UIP 306. Generally, the second processing device 304 may not include the UIP 306 because in that instance the UIP 306 would be unable or less able to isolate the second processing device 304 from the first processing device 302.

The keyboard 308, the pointing device 310, and the touch screen controller 314 are physically connected to the UIP 306 via various connections. The display 312 is thus indirectly connected to the UIP 306 via the touch screen controller 314 and connections 350, 352.

The Keyboard

In general, the UIP 306 receives codes from the keyboard 308, translates the codes, and sends the translated codes to whichever of the first or the second processing devices 302, 304 has focus.

The UIP 306 receives data, e.g., codes and protocol data, from the keyboard 308 over connection 338. The connection 338 may be a serial connection, such as an RS-232 connection. The UIP 306 may translate codes received from the keyboard 308 into codes that are in formats that are compatible with the FHP 302 or the EP 304, as applicable. The UIP 306 may then send the translated codes to whichever of the first or second processing devices 302, 304 has focus. If the FHP 302 has focus, the UIP 306 sends the translated codes (now being of a compatible format to that of the FHP 302) to the FHP 302 via connection 322, which may be a serial connection. If the EP 304 has focus, the UIP 306 sends the translated codes (now being of a compatible format to that of the EP 304) to the EP 304 via connection 330, which may be a USB connection.

As discussed above, the UIP 306 communicates at least some protocol data on connections 322, 330 so that the FHP 302 and the EP 304 are programmed to perceive that they have connections with the keyboard 308, even when the devices 302, 304 do not have focus.

The codes sent from the keyboard 308 to the UIP 306 may generally include press and release codes. A press code is sent when (and while) a user presses a key (or keys) on the keyboard 308, while a release code is sent when a user stops pressing a key (or keys) on the keyboard 308.

As discussed above, the keyboard 308 may include a key 318, which, when pressed (or released) by a user causes switch command(s) in the form of key code(s) (press or release codes) to be sent to the UIP 306. A combination of keys (e.g., "CTRL-SHIFT") pressed together or in sequence, rather than a single key may also be used to trigger the switch command. The UIP 306 may be configured to interpret a particular key code or combination of key codes (simultaneous or sequential) as a switch command. The recognized key code(s) may cause the UIP 306 to switch focus from whichever processing device has focus to whichever processing device does not have focus.

The UIP 306 may save and retrieve configuration data, such as the state of a key on the keyboard 308, such as the "CAPS LOCK" key, so that when focus returns to a particular processing device, the UIP 306 can recall what the state of the key was at the time focus left that particular processing device.

Figure 6:
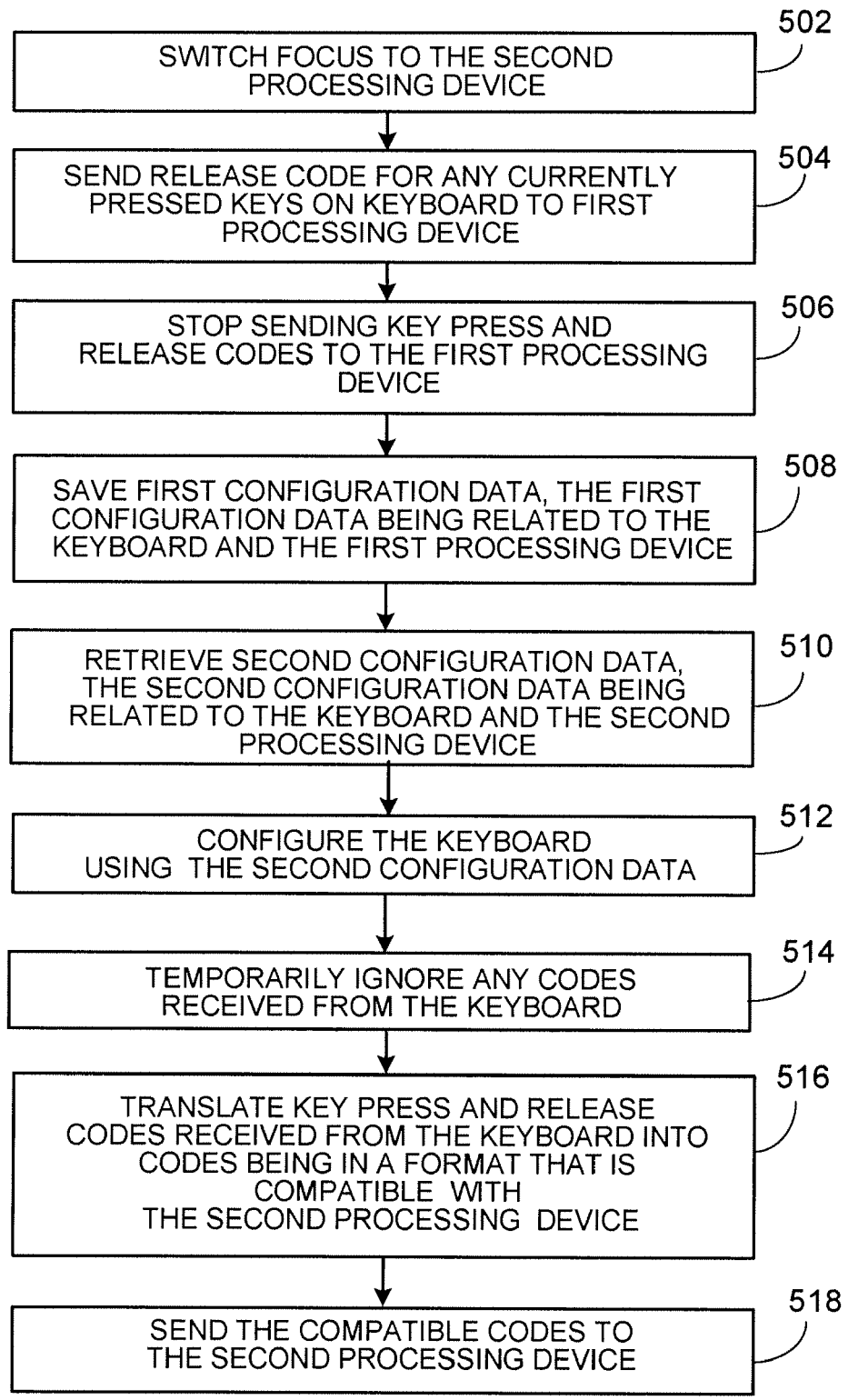
FIG. 6 is a flow diagram showing an example process of a user interface processing device relating to use of a keyboard.

FIG. 6 is a flow diagram showing an example process 500 of a user interface processing device such as the UIP 306 as relates to switching focus between processing devices and managing communications between the keyboard 308 and the processing device that has focus.

Processing begins, for example, where the UIP 306 switches (502) focus to the second processing device 304 from the first processing device 302 (502). Thus, the EP 304 has focus.

The UIP 306 then sends (504) a release code for any currently pressed keys on the keyboard 308 to the first processing device 302, which previously had focus. This may smooth the effects of a sudden transition that may occur when a user is in mid-keystroke, such as when focus was switched in response to a control request or a request for focus sent by the FHP 302 to the UIP 306 in response to, e.g., an alarm. [Note that in FIG. 6 focus switches from the FHP 302 to the EP 304.] This is opposed to a situation where a user may actively request a change in focus by, e.g., pressing a key on the keyboard 308 that causes a switch command to be sent to the UIP 306, and the user may likely not be pressing other keys at the time of requesting that focus be switched.

The UIP 306 then stops sending (506) key press and release codes to the first processing device 302, which previously had focus. That is, if a user of the HD device 300 presses any more keys on the keyboard 308, the UIP 306 will not send the key codes to the FHP 302.

The UIP 306 then saves (508) first configuration data. The first configuration data are related to the keyboard 308 and the first processing device 302, which previously had focus. The first configuration data may include the state of a "CAPS LOCK" key on the keyboard 308. The UIP 306 may save a current state of the "CAPS LOCK" key (in, e.g., memory 358) as a last state of the first processing device 302. In this way, the state of the "CAPS LOCK" key is preserved so that the state may be retrieved the next time that the first processing device 302 has focus. For example, if the user had been typing with "CAPS LOCK" on when the change in focus from the FHP 302 to the EP 304 occurred, then the next time the focus is switched back to the FHP 302, the keyboard would once again have "CAPS LOCK" on, even if the state of the "CAPS LOCK" had been off (or not pressed) when the EP 304 had focus.

The UIP 306 then retrieves (510) second configuration data. The second configuration data are related to the keyboard 308 and the second processing device 304. The second configuration data may include the state of a "CAPS LOCK" key on the keyboard 308. The UIP 306 may retrieve the state of the "CAPS LOCK" key (from, e.g., memory 358) corresponding to when the second processing device 304 last had focus.

The UIP 306 then configures (512) the keyboard 308 using the second configuration data. The UIP 306 may send a command to the keyboard 308 to configure the keyboard 308 so that the keyboard 308 matches the state of the "CAPS LOCK" key from the last time the second processing device 304 had focus. This might involve causing a light on the keyboard 308 that corresponds to the state of the "CAPS LOCK" key to be turned on or off, or causing the keyboard 308 to send a code corresponding to a state of the "CAPS LOCK" key.

The UIP 306 then temporarily ignores (514) any codes received from the keyboard 308. The UIP 306 may ignore codes corresponding to user interactions with the keyboard 308 for X seconds, where X is, e.g., two or three seconds. This may also smooth the effects of a sudden transition that may occur when, e.g., focus was switched in response to a control request or a request for focus sent by the FHP 302 to the UIP 306 in response to, e.g., an alarm. [Note that in FIG. 6 focus switches from the FHP 302 to the EP 304.]

The UIP 306 then translates (516) key press and release codes received from the keyboard 308 into codes being in a format that is compatible with the second processing device 304. The EP 304 now has focus, and the UIP 306 manages communications between the keyboard 308 and the EP 304 by, e.g., translating codes from a protocol or format sent by the keyboard 308 to a protocol or format that is compatible with the EP 304. It may be that not all codes sent by the keyboard 308 require translation by the UIP 306.

The UIP 306 then sends (518) the compatible codes (e.g., the translated codes) to the second processing device 304. The UIP 306 may send all key press and release codes from the keyboard 308 over connection 330 to the EP 304. The UIP 306 may continue to manage communications (e.g., 516, 518) between the keyboard 308 and the EP 304 while the EP 304 has focus and until focus is switched to the FHP 302.

Although FIG. 6 shows an example process 500 in the instance where focus is switched from the first processing device 302 to the second processing device 304, the process 500 is easily adjusted to illustrate the instance where focus is switched from the second processing device 304 to the first processing device 302.

The Pointing Device

In general, the UIP 306 receives codes from the pointing device 310, translates the codes, and sends the translated codes to whichever of the first or the second processing devices 302, 304 has focus.

The UIP 306 receives data, e.g., codes and protocol data, from the pointing device 310 (e.g., a touchpad, a mouse, or a trackball) over connection 340. The connection 340 may be a serial connection, such as an RS-232 connection. The UIP 306 may translate codes received from the pointing device 310 into codes that are in formats that are compatible with the FHP 302 or the EP 304, as applicable. The UIP 306 may then send the translated codes to whichever of the first or second processing devices 302, 304 has focus. If the FHP 302 has focus, the UIP 306 sends the translated codes (now being of a compatible format to that of the FHP 302) to the FHP 302 via connection 324, which may be a serial connection. If the EP 304 has focus, the UIP 306 sends the translated codes (now being of a compatible format to that of the EP 304) to the EP 304 via connection 332, which may be a USB connection.

As discussed above, the UIP 306 communicates at least some protocol data on connections 324, 332 so that the FHP 302 and the EP 304 are programmed to perceive that they have connections with the pointing device 310, even when the devices 302, 304 do not have focus.

The pointing device codes sent from the pointing device 310 to the UIP 306 may generally include relative x-y coordinates, e.g., coordinates that define a movement of a user's digit (e.g. a finger) along a surface of the pointing device (e.g., in the case of a touchpad), or a movement of the pointing device 310 along a surface (e.g., in the case of a mouse); or press and release codes, or both. A press code is sent when (and while) a user touches a button (or buttons) on the pointing device 310, while a release code is sent when a user stops touching a button (or buttons) on the pointing device 310.

The pointing device 310 may be configured to send a switch command to the UIP 306. The UIP 306 may be configured to interpret a particular pointing device code or combination of codes (simultaneous or sequential) as a switch command. The recognized pointing device code(s) may cause the UIP 306 to switch focus from whichever processing device has focus to whichever processing device does not have focus.

Figure 7:
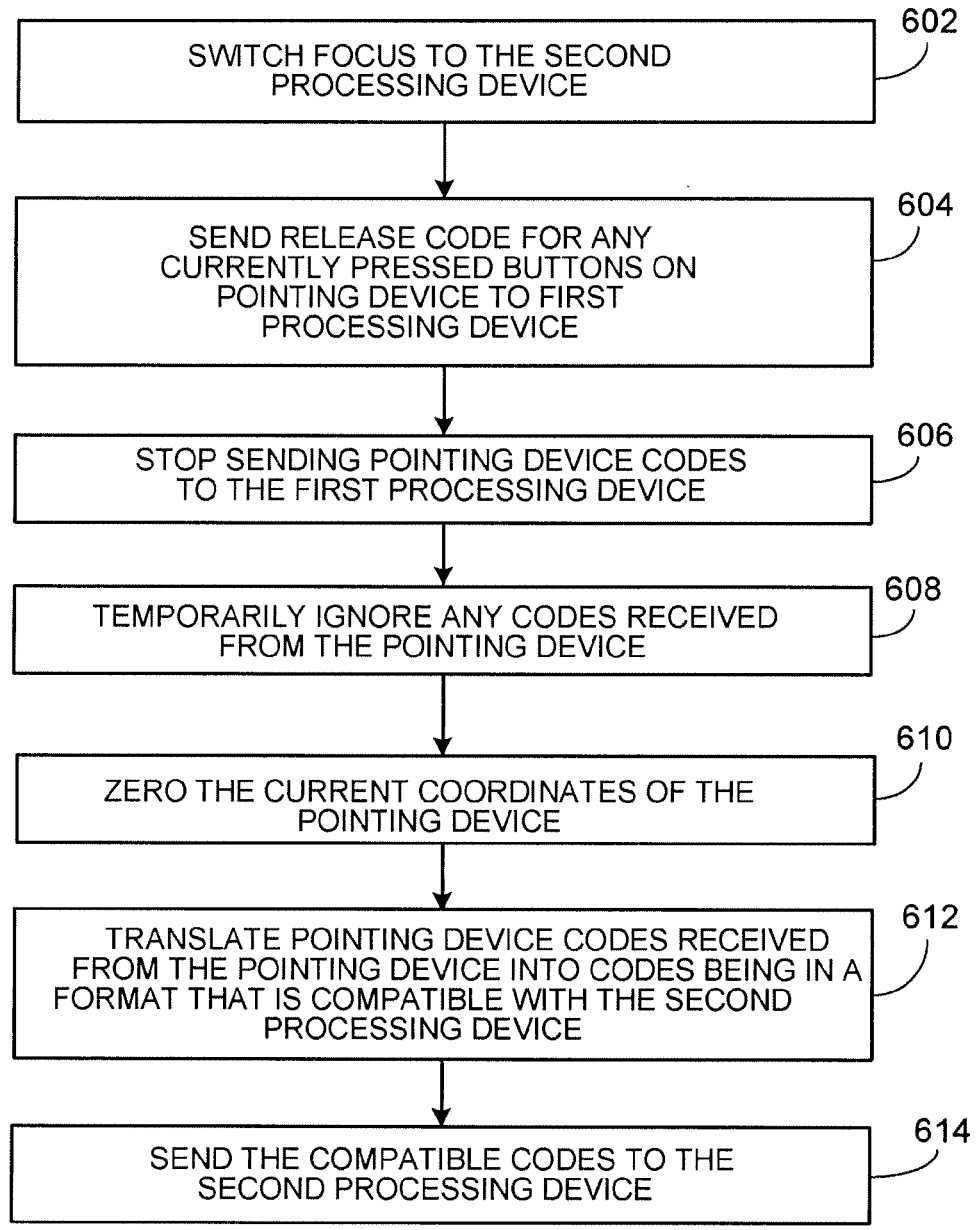
FIG. 7 is a flow diagram showing an example process of a user interface processing device relating to use of a pointing device.

FIG. 7 is a flow diagram showing an example process 600 of a user interface processing device such as the UIP 306 as relates to switching focus between processing devices and managing communications between the pointing device 310 and the processing device that has focus.

Processing begins, for example, where the UIP 306 switches focus to the second processing device 304 from the first processing device 302 (602). Thus, the EP 304 has focus.

The UIP 306 then sends (604) a release code for any currently pressed buttons on the pointing device 310 to the first processing device 302, which previously had focus. This may smooth the effects of a sudden transition that may occur when a user is in the middle of pressing a button, such as when focus was switched in response to a control request or a request for focus was sent by the FHP 302 to the UIP 306 in response to, e.g., an alarm. [Note that in FIG. 7 focus switches from the FHP 302 to the EP 304.] This is opposed to a situation where a user may actively request a change in focus by, e.g., pressing a button on the pointing device 310, for, e.g., 5 seconds, that may cause a switch command to be sent to the UIP 306.

The UIP 306 then stops sending (606) pointing device codes to the first processing device 302, which previously had focus. That is, if a user of the HD device 300 interacts with the pointing device 310, the UIP 306 will not send any codes that may result to the FHP 302.

The UIP 306 then temporarily ignores (608) any codes received from the pointing device 310. The UIP 306 may ignore codes corresponding to user interactions with the pointing device 310 for X seconds, where X is, e.g., two or three seconds. This may also smooth the effects of a sudden transition in focus.

The UIP 306 then initializes (610) the current coordinates of the pointing device 310. The pointing device codes sent from the pointing device 310 to the UIP 306 may generally include relative x-y coordinates, e.g., coordinates that define a movement of a user's digit (e.g. a finger) along a surface of the pointing device, or a movement of the pointing device 310 along a surface. Initializing or "zeroing" these relative x-y coordinates would create a new initial coordinate from which a movement (of, e.g., a user's digit or the pointing device) may be tracked. In this way, the UIP 306 is in a position to provide the processing device that has been given focus (here the EP 304) with new pointing device codes.

The UIP 306 then translates (612) pointing device codes received from the pointing device 310 into codes being in a format that is compatible with the second processing device 304. The EP 304 now has focus, and the UIP 306 manages communications between the pointing device 310 and the EP 304 by, e.g., translating codes from a protocol or format sent by the pointing device 310 to a protocol or format that is compatible with the EP 304. It may be that not all codes sent by the pointing device 310 require translation by the UIP 306.

The UIP 306 then sends (614) the compatible codes (e.g., the translated codes) to the second processing device 304. The UIP 306 may send all pointing device codes from the pointing device 310 over connection 332 to the EP 304. The UIP 306 may continue to manage communications (e.g., 612, 614) between the pointing device 310 and the EP 304 while the EP 304 has focus and until focus is switched to the FHP 302.

Although FIG. 7 shows an example process 600 in the instance where focus is switched from the first processing device 302 to the second processing device 304, the process 600 is easily adjusted to illustrate the instance where focus is switched from the second processing device 304 to the first processing device 302.

The Display With Touch Screen and the Touch Screen Controller

In general, the UIP 306 causes the display 312 to be switched to whichever of the first or the second processing devices 302, 304 has focus.

As mentioned above, the display 312 is connected to the digital video switch 316 via connection 342, which is in turn connected to the UIP 306, the FHP 302, and the EP 304 via respective connections 344, 346, 348.

The display 312 may include a screen with an LCD (liquid crystal display) display.

The digital video switch 316 receives video streams from the FHP 302 and the EP 304 via respective connections 346, 348. The UIP 306 controls the digital video switch 316 via connection 344 and causes the switch 316 to switch the display 312 (via connection 342) to the video stream of whichever of the first or the second processing devices 302, 304 has focus. The display 312 may show only the video stream corresponding to the processing device that has focus.

In an implementation, the digital video switch supports picture in picture so that the display 312 may shows more than one video stream at one time, although the video stream corresponding to the processing device that has focus may generally be larger on the display 312.

When the UIP 306 switches focus from one processing device to another, the digital video switch 316 may support a fast or slow dissolve from one video stream to another. For example, upon a change of focus from one processing device to another, the switch 316 may fade out the video stream corresponding to the processing device that has lost focus and fade in the video stream corresponding to the processing device that has gained focus. The "fade in" and "fade out" processes may overlap one another. The switch between one video stream to another as shown on display 312 may be a "soft" switch rather than a "hard" switch, where a soft switch is a less than instantaneous so that a user is given, for example, a half second to adjust to the display change.

The digital video switch 316 may scale signals in the incoming video streams to match the resolution of the display 312, if, for example, the video streams for one of the processing devices is set at a different resolution than the display 312.

The touch screen controller 314 is connected to the display 312 via connection 350, and to the UIP 306 via connection 352. In other implementations, the touch screen controller 314 may be included in the UIP 306 or the display 312.

In general, the UIP 306 receives codes from the touch screen controller 314 according to a particular configuration of the touch screen controller 314 and sends the codes to whichever of the first or the second processing devices 302, 304 has focus. After the UIP 306 switches focus from the first processing device 302 to the second processing device 304, or vice versa, the UIP 306 reconfigures the touch screen controller 314 according to which device 302, 304 has been given focus, and, thereafter, the codes from the touch screen controller 314 are compatible with the device 302, 304 that has focus.

The UIP 306 receives data, e.g., codes and protocol data, from the touch screen controller 314 over connection 352. The touch screen controller 314 may be configured to be compatible with whichever of the first or second processing devices 302, 304 has focus, so that codes and protocol data sent from the touch screen controller 314 are compatible with the processing device that has focus. The connection 352 may be a serial connection, such as an RS-232 connection. The UIP 306 may send the codes to whichever of the first or second processing devices 302, 304 has focus. If the FHP 302 has focus, the UIP 306 sends the codes to the FHP 302 via connection 328, which may be a serial connection. If the EP 304 has focus, the UIP 306 sends the codes to the EP 304 via connection 336, which may be a USB connection or a serial connection.

As discussed above, the UIP 306 communicates at least some protocol data on connections 328, 336 so that the FHP 302 and the EP 304 are programmed to perceive that they have connections with the display 312 (and the touch screen controller 314), even when the devices 302, 304 do not have focus.

The touch screen codes sent from the touch screen controller 314 to the UIP 306 may include absolute x-y coordinates, e.g., coordinates that correspond to a position of a user's digit (e.g., a finger) on the touch screen of the display 312. The touch screen codes may include commands rather than x-y coordinates, based on a mapping by the touch screen controller of coordinates to particular commands. Codes may be sent that include, e.g., absolute x-y coordinates accompanied by an indication corresponding to an initial touch of the user's digit on the touch screen, a streaming touch of the user's digit on the touch screen (e.g., a movement of the user's digit while touching the touch screen), or to a removal of the user's digit from the touch screen. The particular configuration of the touch screen controller 314 (e.g., FHP 302 compatible or EP 304 compatible) provided by the UIP 306 may generally determine how codes can be assigned to particular user interactions with the touch screen of the display 312, both in terms of what constitutes a selection by the user of a particular item on the touch screen as well as what particular mapping and scale may be used for the touch screen. For example, the touch screen controller 314 may assign an initial touch of the user's digit at a particular place on the touch screen to a particular x-y coordinate based on a mapping of the touch screen in the configuration of the controller 314 and the controller 314 may send the coordinate code to the UIP 306.

The touch screen controller 314 may be configured to send a switch command to the UIP 306. The UIP 306 may be configured to interpret a particular touch screen code or combination of codes (simultaneous or sequential) as a switch command. The recognized touch screen code(s) may cause the UIP 306 to switch focus from whichever processing device has focus to whichever processing device does not have focus.

Figure 8:
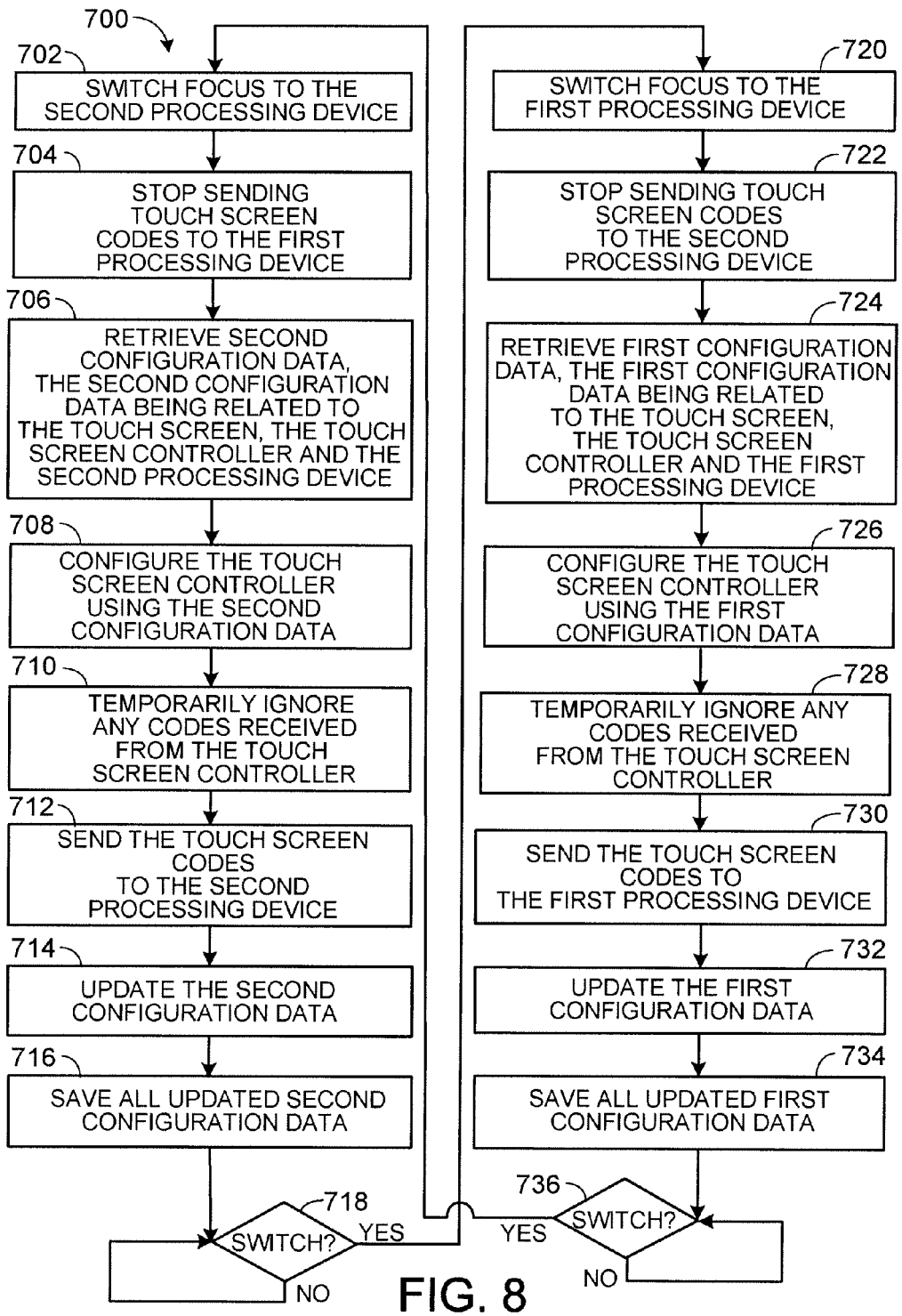
FIG. 8 is a flow diagram showing an example process of a user interface processing device relating to use of a touch screen.

FIG. 8 is a flow diagram showing an example process 700 of a user interface processing device such as the UIP 306 as relates to switching focus between processing devices and managing communications between the display 312 with touch screen (and the touch screen controller 314) and the processing device that has focus.

Processing begins, for example, where the UIP 306 switches focus to the second processing device 304 from the first processing device 302 (702). Thus, the EP 304 has focus.

The UIP 306 then stops sending (704) touch screen codes to the first processing device 302, which previously had focus. That is, if a user of the HD device 300 presses the touch screen of the display 312, the UIP 306 will not send the touch screen code(s) to the FHP 302.

The UIP 306 then retrieves (706) second configuration data. The second configuration data are related to the touch screen of the display 312, the touch screen controller 314, and the second processing device 304. The second configuration data may include a second configuration state of the touch screen controller 314 that corresponds to the second processing device 304. The second configuration state may have been saved in a previous period in which the second processing device 304 last had focus. The UIP 306 may retrieve the second configuration state from, e.g., memory 358.

The UIP 306 then configures (708) the touch screen controller 314 using the second configuration data. The UIP 306 may send one or more commands to the touch screen controller 314 to configure (or reconfigure) the touch screen controller 314 so that the touch screen controller 314 matches the retrieved (706) second configuration state from the last time the second processing device 304 had focus.

The UIP 306 then temporarily ignores (710) any codes received from the touch screen controller 314. The UIP 306 may ignore codes corresponding to user interactions with the touch screen of the display 312 for X seconds, where X is, e.g., two or three seconds. This may also smooth the effects of a sudden transition that may occur when, e.g., focus was switched in response to a control request or a request for focus sent by the FHP 302 to the UIP 306 in response to, e.g., an alarm. [Note that in this portion of FIG. 8 focus switches from the FHP 302 to the EP 304.]

In an implementation, the UIP 306 may then translate (not shown in FIG. 8) touch screen codes received from the touch screen controller 314 into codes being in a format that is compatible with the second processing device 304. Due to the configuration (708) of the touch screen controller 314 by the UIP 306, however, the touch screen codes from the touch screen controller 314 may generally already be in a format that is compatible with the second processing device 304 and may not require translation by the UIP 306.

The UIP 306 then sends (712) the compatible touch screen codes (untranslated or otherwise) to the second processing device 304. The UIP 306 may send all touch screen codes the touch screen controller 314 over connection 336 to the EP 304.

The UIP 306 then updates (714) the second configuration data. The UIP 306 may update the second configuration state of the touch screen controller 314 that corresponds to the second processing device 304 using touch screen codes sent by the second processing device 304 to the UIP 306.

The UIP 306 then saves (716) the (e.g., updated) second configuration data. The UIP 306 may save (in, e.g., memory 358) a current second configuration state of the touch screen controller 314 corresponding to the second processing device 304. In this way, the second configuration state of the touch screen controller 314 is preserved so that the state may be retrieved the next time that the second processing device 304 has focus.

The UIP 306 may continue to manage communications (e.g., 712, 714) between the touch screen controller 314 and the EP 304 while the EP 304 has focus and until focus is switched to the FHP 302.

The UIP 306 then determines (718) whether to switch focus from the second processing device 304 to the first processing device 302. To accomplish this decision, the UIP 306 may use a similar process to process 400 shown in FIG. 5. Note that the UIP 306 "determining" whether to switch focus may include responding to a switch command or a control request or request for focus that the UIP 306 generally may not be permitted to ignore.

If the UIP 306 determines that focus should not be switched (a "NO" from decision 718 in FIG. 8), processing may return to the decision 718 or, to a point earlier in the process 700 (e.g., 712, 714, 716).

If the UIP 306 determines that focus should be switched from the second processing device 304 to the first processing device 302 (a "YES" from decision 718 in FIG. 8), processing continues where the UIP 306 switches focus to the first processing device 302 from the second processing device 304 (720). Thus, the FHP 302 has focus.

The UIP 306 then stops sending (722) touch screen codes to the second processing device 304, which previously had focus. That is, if a user of the HD device 300 presses the touch screen of the display 312, the UIP 306 will not send the touch screen code(s) to the EP 304.

The UIP 306 then retrieves (724) first configuration data. The first configuration data are related to the touch screen of the display 312, the touch screen controller 314, and the first processing device 302. The first configuration data may include a first configuration state of the touch screen controller 314 that corresponds to the first processing device 302. The first configuration state may have been saved in a previous period in which the first processing device 302 last had focus. The UIP 306 may retrieve the first configuration state from, e.g., memory 358.

The UIP 306 then configures (726) the touch screen controller 314 using the first configuration data. The UIP 306 may send one or more commands to the touch screen controller 314 to configure (or reconfigure) the touch screen controller 314 so that the touch screen controller 314 matches the retrieved (724) first configuration state from the last time the first processing device 302 had focus.

The UIP 306 then temporarily ignores (728) any codes received from the touch screen controller 314. The UIP 306 may ignore codes corresponding to user interactions with the touch screen of the display 312 for X seconds, where X is, e.g., two or three seconds. This may also smooth the effects of a sudden transition that may occur when, e.g., focus was switched in response to a control request or a request for focus sent by the FHP 302 to the UIP 306 in response to, e.g., an alarm.

In an implementation, the UIP 306 may then translate (not shown in FIG. 8) touch screen codes received from the touch screen controller 314 into codes being in a format that is compatible with the first processing device 302. Due to the configuration (726) of the touch screen controller 314 by the UIP 306, however, the touch screen codes from the touch screen controller 314 may generally already be in a format that is compatible with the first processing device 302 and may not require translation by the UIP 306.

The UIP 306 then sends (730) the compatible touch screen codes (untranslated or otherwise) to the first processing device 302. The UIP 306 may send all touch screen codes the touch screen controller 314 over connection 328 to the FHP 302.

The UIP 306 then updates (732) the first configuration data. The UIP 306 may update the first configuration state of the touch screen controller 314 that corresponds to the first processing device 304 using touch screen codes sent by the first processing device 304 to the UIP 306.

The UIP 306 then saves (734) the (e.g., updated) first configuration data. The UIP 306 may save (in, e.g., memory 358) a current first configuration state of the touch screen controller 314 corresponding to the first processing device 302. In this way, the first configuration state of the touch screen controller 314 is preserved so that the state may be retrieved the next time that the first processing device 302 has focus.

The UIP 306 may continue to manage communications (e.g., 730, 732) between the touch screen controller 314 and the FHP 302 while the FHP 302 has focus and until focus is switched to the EP 304.

The UIP 306 then determines (736) whether to switch focus from the first processing device 302 to the second processing device 304. To accomplish this decision, the UIP 306 may use a similar process to process 400 shown in FIG. 5. Note that the UIP 306 "determining" whether to switch focus may include responding to a switch command or a control request or request for focus that the UIP 306 generally may not be permitted to ignore.

If the UIP 306 determines that focus should not be switched (a "NO" from decision 736 in FIG. 8), processing may return to the decision 736 or, to a point earlier in the process 700 (e.g., 730, 732, 734).

If the UIP 306 determines that focus should be switched from the first processing device 302 to the second processing device 304 (a "YES" from decision 736 in FIG. 8), processing continues where the UIP 306 switches focus to the second processing device 304 from the first processing device 302 (702). Thus, the EP 304 has focus and processing may continue as described above.

The Audio Device

The audio device 362 of the HD device 300 may include an audio amplifier and one or more loudspeakers. The audio device 362 may operate with the EP 304 via connection 364 and may, when the EP 304 has focus, be controlled by the EP 304 and may output audio at the direction of the EP 304. When the UIP 306 switches focus to the FHP 302 from the EP 304, or when the FHP 302 first has focus, the UIP 306 may send a mute command to the audio device 362 via connection 366. The mute command may turn the sound off of the audio device 362 so that the EP 304 no longer controls the audio device 362. When the EP 304 has focus, the UIP 306 may cede control of the audio device 362 to the EP 304.

Although the processes described herein have been discussed in terms of hemodialysis and of hemodialysis machines and devices, the processes described herein could, alternatively or additionally, be used in, and applied to, peritoneal dialysis and peritoneal dialysis machines and devices.

In general, when a user interface device is said to control or affect operation of a processing device, it is understood that user interactions with a user interface device may cause the user interface device to control or affect such operation and thus the interactions themselves may also be said to control or affect such operation.

In general, when referring to a situation in which focus is said to be switched to one processing device from another processing device, it is understood that this language may also refer to a situation in which one processing device has focus, without focus necessarily having been switched from another processing device.

Connections may be wired and/or wireless connections. When one component is said to be connected to another component, the component may be directly connected or indirectly connected (via, e.g., still another component) to the other component.

The processes described herein and their various modifications (hereinafter "the processes"), are not limited to the hardware and software described above. All or part of the processes can be implemented, at least in part, via a computer program product, e.g., a computer program tangibly embodied in an information carrier, such as one or more machine-readable media or a propagated signal, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subrouting, or other unit suitable for use in a computing environment. A computer program can be deployed to be executed on one computer or on multiple computers at one site or distributed across multiple sites and interconnected by a network.

Actions associated with implementing all or part of the processes can be performed by one or more programmable processing devices executing one or more computer programs to perform the functions of the processes. All or part of the processes can be implemented as, special purpose logic circuitry, e.g., an FPGA (field programmable gate array) and/or an ASIC (application-specific integrated circuit).

Processing devices suitable for the execution of a computer program include, by way of example, both general and special purpose microprocessors, and any one or more processors of any kind of digital computer. Generally, a processing device will receive instructions and data from a read-only memory or a random access memory or both. Components of a computer include one or more processing devices for executing instructions and one or more memory devices for storing instructions and data.

Components of different implementations described herein may be combined to form implementations not specifically set forth above. Other implementations not specifically described are also within the scope of the following claims.

What is claimed is:

1. A method performed by one or more user interface processing devices, of sharing one or more user interface devices between a first processing device and a second processing device, wherein a dialysis device comprises the one or more user interface processing devices, the first processing device, and the second processing device, the method comprising:
   switching focus from the first processing device to the second processing device or from the second processing device to the first processing device,
   wherein the first processing device is configured to monitor dialysis functions of the dialysis device;
   wherein, when the first processing device has focus:
      managing first communications between the one or more user interface devices and the first processing device; and
      permitting the one or more user interface devices to affect operation of the first processing device;
   and, when the second processing device has focus:
      managing second communications between the one or more user interface devices and the second processing device, wherein managing second communications between the one or more user interface devices and the second processing device comprises
      translating first codes received from the one or more user interface devices into second codes,
      sending the second codes to the second processing device, and
      switching focus from the second processing device to the first processing device if no first codes are received from the one or more user interface devices for a first period of time; and
      permitting the one or more user interface devices to affect operation of the second processing device.

2. The method of claim 1, wherein the dialysis device further comprises the one or more user interface devices.

3. The method of claim 1, further comprising:
   switching focus from the second processing device to the first processing device responsively to a request.

4. The method of claim 3, further comprising:
   receiving the request from the first processing device;
   wherein the request is based on monitoring of the dialysis device by the first processing device.

5. The method of claim 4, wherein the request is responsive to a dialysis device alarm.

6. The method of claim 3, wherein the request is indicative of at least one of a first condition of the dialysis device or a second condition of a patient receiving treatment from the dialysis device.

7. The method of claim 1, wherein switching focus comprises:
   switching focus from the first processing device to the second processing device or from the second processing device to the first processing device responsively to a switch command received from one user interface device of the one or more user interface devices.

8. The method of claim 7, wherein the one user interface device comprises a keyboard; and
   wherein the switch command comprises at least one of a press code or a release code, the press code or the release code corresponding to a key on the keyboard.

9. The method of claim 1, wherein the second processing device comprises a microprocessor embedded within the dialysis device.

10. The method of claim 1, wherein the first processing device comprises the one or more user interface processing devices.

11. The method of claim 1, further comprising:
    sending first and second protocol data to the first and second processing devices, respectively, so that the first and second processing devices are configured to maintain one or more respective connections with the one or more user interface devices, irrespective of which processing device of the first and second processing devices has focus.

12. The method of claim 1, wherein the one or more user interface devices comprise a keyboard.

13. The method of claim 12, further comprising:
    interpreting one or more codes as a switch command; and
    responsively to the switch command, switching focus from the first processing device to the second processing device or from the second processing device to the first processing device;
    wherein the keyboard comprises a key, and the keyboard is configured to send the one or more codes to the one or more user interface processing devices when the key is pressed.

14. The method of claim 1, wherein the one or more user interface devices comprise a pointing device; wherein the pointing device comprises at least one of a mouse, a trackball, or a touchpad.

15. The method of claim 1, wherein the one or more user interface devices comprise a display, the display comprising a touch screen.

16. The method of claim 1, further comprising:
    isolating the second processing device from the first processing device so that if the second processing device experiences a condition, the first processing device and the dialysis functions of the dialysis device are not affected by the condition.

17. The method of claim 16, wherein the condition comprises at least one of a shut down of the second processing device or a computer virus.

18. The method of claim 16, further comprising:
    restarting the second processing device without affecting the first processing device and the dialysis functions of the dialysis device.

19. The method of claim 1, wherein managing second communications between the one or more user interface devices and the second processing device comprises:
    translating first codes received from the one or more user interface devices into second codes, the second codes being of one or more respective formats, the one or more respective formats being compatible with the second processing device; and
    sending the second codes to the second processing device.

20. The method of claim 1, wherein managing first communications between the one or more user interface devices and the first processing device comprises:
    translating first codes received from the one or more user interface devices into second codes, the second codes being of one or more respective formats, the one or more respective formats being compatible with the first processing device; and
    sending the second codes to the first processing device.

21. The method of claim 1, further comprising:
prior to switching focus from the first processing device to the second processing device:
translating first codes received from the one or more user interface devices into second codes, the second codes being of one or more respective first formats, the one or more respective first formats being compatible with the first processing device; and
sending the second codes to the first processing device; and
after switching focus from the first processing device to the second processing device:
stopping sending the second codes to the first processing device;
temporarily ignoring any codes received from the one or more user interface devices;
translating third codes received from the one or more user interface devices into fourth codes, the fourth codes being of one or more respective second formats, the one or more respective second formats being compatible with the second processing device; and
sending the fourth codes to the second processing device.

22. The method of claim 21, further comprising:
after switching focus from the first processing device to the second processing device:
saving first configuration data, the first configuration data being related to the one or more user interface devices and the first processing device;
retrieving second configuration data, the second configuration data being related to the one or more user interface devices and the second processing device; and
configuring the one or more user interface devices using the second configuration data.

23. The method of claim 22, wherein the one or more user interface devices comprise a keyboard, the keyboard comprising a key;
wherein the first and third codes comprise press codes and release codes; and
wherein the first configuration data comprise a first state of the key, the first state being prior to switching focus from the first processing device to the second processing device.

24. The method of claim 23, wherein the second configuration data comprise a second state of the key, the second state being from a previous period in which the second processing device had focus, the previous period being prior to a present period in which the second processing device has focus.

25. The method of claim 21, wherein the one or more user interface devices comprise a pointing device, the pointing device comprising one or more keys;
wherein the first and third codes comprise pointing device codes, the pointing device codes corresponding to at least one of movement of the pointing device, movement of a digit along a surface of the pointing device, or press codes and release codes corresponding to the one or more keys.

26. The method of claim 25, wherein the pointing device comprises a touchpad.

27. The method of claim 1, further comprising:
prior to switching focus from the first processing device to the second processing device:
saving first configuration data, the first configuration data being related to the one or more user interface devices and the first processing device; and
after switching focus from the first processing device to the second processing device:
retrieving second configuration data, the second configuration data being related to the one or more user interface devices and the second processing device;
configuring the one or more user interface devices using the second configuration data; and
saving the second configuration data.

28. The method of claim 27, further comprising:
prior to switching focus from the first processing device to the second processing device:
sending first codes to the first processing device, the first codes being of one or more respective first formats, the one or more respective first formats being related to the first configuration data;
and
after switching focus from the first processing device to the second processing device:
stopping sending the first codes to the first processing device;
temporarily ignoring any codes received from the one or more user interface devices; and
sending second codes to the second processing device, the second codes being of one or more respective second formats, the one or more respective second formats being related to the second configuration data.

29. The method of claim 28, wherein the one or more user interface devices comprise a display and a touch screen controller, the display comprising a touch screen;
wherein the first and second codes comprise touch screen codes received from the touch screen controller; and
wherein the first configuration data comprise a first configuration state of the touch screen controller corresponding to the first processing device, the first configuration state being prior to switching focus from the first processing device to the second processing device.

30. The method of claim 29, wherein the second configuration data comprise a second configuration state of the touch screen controller corresponding to the second processing device, the second configuration state being from a previous period in which the second processing device had focus, the previous period being prior to a present period in which the second processing device has focus.

31. The method of claim 29, wherein the one or more user interface processing devices comprise the touch screen controller.

32. The method of claim 29, wherein temporarily ignoring any codes received from the one or more user interface devices comprises:
temporarily ignoring any codes received from the touch screen controller relating to interactions of a user with the touch screen.

33. The method of claim 1, further comprising:
prior to switching focus from the second processing device to the first processing device:
translating first codes received from the one or more user interface devices into second codes, the second codes being of one or more respective second formats, the one or more respective second formats being compatible with the second processing device; and
sending the second codes to the second processing device;
and
after switching focus from the second processing device to the first processing device:

stopping sending the second codes to the second processing device;
temporarily ignoring any codes received from the one or more user interface devices; and
translating third codes received from the one or more user interface devices into fourth codes, the fourth codes being of one or more respective first formats, the one or more respective first formats being compatible with the first processing device; and
sending the fourth codes to the first processing device.

34. The method of claim 33, further comprising:
after switching focus from the second processing device to the first processing device:
saving second configuration data, the second configuration data being related to the one or more user interface devices and the second processing device;
retrieving first configuration data, the first configuration data being related to the one or more user interface devices and the first processing device; and
configuring the one or more user interface devices using the first configuration data.

35. The method of claim 1, further comprising:
prior to switching focus from the second processing device to the first processing device:
saving second configuration data, the second configuration data being related to the one or more user interface devices and the second processing device;
and
after switching focus from the second processing device to the first processing device:
retrieving first configuration data, the first configuration data being related to the one or more user interface devices and the first processing device;
configuring the one or more user interface devices using the first configuration data; and
saving the first configuration data.

36. The method of claim 35, further comprising:
prior to switching focus from the second processing device to the first processing device:
sending second codes to the second processing device, the second codes being of one or more respective second formats, the one or more respective second formats being related to the second configuration data;
and
after switching focus from the second processing device to the first processing device:
stopping sending the second codes to the second processing device;
temporarily ignoring any codes received from the one or more user interface devices;
sending first codes to the first processing device, the first codes being of one or more respective first formats, the one or more respective first formats being related to the first configuration data.

37. The method of claim 1, further comprising:
after switching focus from the second processing device to the first processing device:
sending a mute command to an audio device,
wherein the dialysis device further comprises the audio device, and wherein when the second processing device has focus, the second processing device is configured to control the audio device.

38. A dialysis device comprising:
one or more user interface devices;
means for monitoring dialysis functions of the dialysis device;
means for performing non-dialysis functions, the non-dialysis functions comprising data entry functions;
means for switching focus from the monitoring means to the performing means or from the performing means to the monitoring means;
means for, when the means for monitoring has focus:
managing first communications between the one or more user interface devices and the means for monitoring; and
permitting the one or more user interface devices to affect operation of the means for monitoring; and
means for, when the means for performing has focus:
managing second communications between the one or more user interface devices and the means for performing, wherein managing second communications between the one or more user interface devices and the second processing device comprises
translating first codes received from the one or more user interface devices into second codes,
sending the second codes to the second processing device, and
switching focus from the second processing device to the first processing device if no first codes are received from the one or more user interface devices for a first period of time; and
permitting the one or more user interface devices to affect operation of the means for performing.

39. One or more machine-readable media storing instructions that are executable to share one or more user interface devices between a first processing device and a second processing device, wherein a dialysis device comprises one or more user interface processing devices, the first processing device, and the second processing device, the instructions for causing the one or more user interface processing devices to:
switch focus from the first processing device to the second processing device or from the second processing device to the first processing device,
wherein the first processing device is configured to monitor dialysis functions of the dialysis device;
wherein, when the first processing device has focus:
manage first communications between the one or more user interface devices and the first processing device: and
permit the one or more user interface devices to affect operation of the first processing device; and
and, when the second processing device has focus:
manage second communications between the one or more user interface devices and the second processing device, wherein managing second communications between the one or more user interface devices and the second processing device comprises
translating first codes received from the one or more user interface devices into second codes,
sending the second codes to the second processing device, and
switching focus from the second processing device to the first processing device if no first codes are received from the one or more user interface devices for a first period of time: and
permit the one or more user interface devices to affect operation of the second processing device.

40. The one or more machine-readable media of claim 39, wherein the instructions further comprise instructions for causing the one or more user interface processing devices to:
switch focus from the second processing device to the first processing device responsively to a request,
wherein the request is responsive to a dialysis device alarm.

41. The one or more machine-readable media of claim 39, wherein the instructions further comprise instructions for causing the one or more user interface processing devices to:
  isolate the second processing device from the first processing device so that if the second processing device experiences a condition, the first processing device and the dialysis functions of the dialysis device are not affected by the condition.

42. The one or more machine-readable media of claim 39, wherein the instructions further comprise instructions for causing the one or more user interface processing devices to:
  prior to switching focus from the first processing device to the second processing device:
    translate first codes received from the one or more user interface devices into second codes, the second codes being of one or more respective first formats, the one or more respective first formats being compatible with the first processing device; and
    send the second codes to the first processing device; and
  after switching focus from the first processing device to the second processing device:
    stop sending the second codes to the first processing device;
    temporarily ignore any codes received from the one or more user interface devices;
    translate third codes received from the one or more user interface devices into fourth codes, the fourth codes being of one or more respective second formats, the one or more respective second formats being compatible with the second processing device; and
    send the fourth codes to the second processing device.

43. The one or more machine-readable media of claim 39, wherein the instructions further comprise instructions for causing the one or more user interface processing devices to:
  prior to switching focus from the first processing device to the second processing device:
    save first configuration data, the first configuration data being related to the one or more user interface devices and the first processing device; and
  after switching focus from the first processing device to the second processing device:
    retrieve second configuration data, the second configuration data being related to the one or more user interface devices and the second processing device;
    configure the one or more user interface devices using the second configuration data; and
    save the second configuration data.

44. The one or more machine-readable media of claim 43, wherein the instructions further comprise instructions for causing the one or more user interface processing devices to:
  prior to switching focus from the first processing device to the second processing device:
    send first codes to the first processing device, the first codes being of one or more respective first formats, the one or more respective first formats being related to the first configuration data; and
  after switching focus from the first processing device to the second processing device:
    stop sending the first codes to the first processing device;
    temporarily ignore any codes received from the one or more user interface devices; and
    send second codes to the second processing device, the second codes being of one or more respective second formats, the one or more respective second formats being related to the second configuration data.

45. A dialysis device configured to share one or more user interface devices between a first processing device and a second processing device, the dialysis device comprising:
  the first processing device;
  the second processing device;
  memory configured to store instructions for execution; and
  one or more user interface processing devices configured to execute the instructions, the instructions for causing the one or more user interface processing devices to:
    switch focus from the first processing device to the second processing device or from the second processing device to the first processing device,
    wherein the first processing device is configured to monitor dialysis functions of the dialysis device;
    wherein, when the first processing device has focus:
      manage first communications between the one or more user interface devices and the first processing device: and
      permit the one or more user interface devices to affect operation of the first processing device; and
    and, when the second processing device has focus:
      manage second communications between the one or more user interface devices and the second processing device, wherein managing second communications between the one or more user interface devices and the second processing device comprises
        translating first codes received from the one or more user interface devices into second codes,
        sending the second codes to the second processing device, and
        switching focus from the second processing device to the first processing device if no first codes are received from the one or more user interface devices for a first period of time: and
      permit the one or more user interface devices to affect operation of the second processing device.

46. The dialysis device of claim 45, further comprising:
  the one or more user interface devices.

47. The dialysis device of claim 45, wherein the instructions further comprise instructions for causing the one or more user interface processing devices to:
  switch focus from the second processing device to the first processing device responsively to a request,
  wherein the request is responsive to a dialysis device alarm.

48. The dialysis device of claim 45, wherein the instructions further comprise instructions for causing the one or more user interface processing devices to:
  isolate the second processing device from the first processing device so that if the second processing device experiences a condition, the first processing device and the dialysis functions of the dialysis device are not affected by the condition.

49. The dialysis device of claim 45, wherein the instructions further comprise instructions for causing the one or more user interface processing devices to:
  prior to switching focus from the first processing device to the second processing device:
    translate first codes received from the one or more user interface devices into second codes, the second codes being of one or more respective first formats, the one or more respective first formats being compatible with the first processing device; and
    send the second codes to the first processing device; and after switching focus from the first processing device to the second processing device:
  stop sending the second codes to the first processing device;
  temporarily ignore any codes received from the one or more user interface devices;
  translate third codes received from the one or more user interface devices into fourth codes, the fourth codes being of one or more respective second formats, the one or more respective second formats being compatible with the second processing device; and
  send the fourth codes to the second processing device.

50. The dialysis device of claim 45, wherein the instructions further comprise instructions for causing the one or more user interface processing devices to:
  prior to switching focus from the first processing device to the second processing device:
    save first configuration data, the first configuration data being related to the one or more user interface devices and the first processing device;
  and
  after switching focus from the first processing device to the second processing device:
    retrieve second configuration data, the second configuration data being related to the one or more user interface devices and the second processing device;
    configure the one or more user interface devices using the second configuration data; and
    save the second configuration data.

51. The dialysis device of claim 50, wherein the instructions further comprise instructions for causing the one or more user interface processing devices to:
  prior to switching focus from the first processing device to the second processing device:
    send first codes to the first processing device, the first codes being of one or more respective first formats, the one or more respective first formats being related to the first configuration data;
  and
  after switching focus from the first processing device to the second processing device:
    stop sending the first codes to the first processing device;
    temporarily ignore any codes received from the one or more user interface devices; and
    send second codes to the second processing device, the second codes being of one or more respective second formats, the one or more respective second formats being related to the second configuration data.

* * * * *

UNITED STATES PATENT AND TRADEMARK OFFICE
CERTIFICATE OF CORRECTION

PATENT NO. : 8,323,503 B2
APPLICATION NO. : 12/137375
DATED : December 4, 2012
INVENTOR(S) : Roland Levin et al.

It is certified that error appears in the above-identified patent and that said Letters Patent is hereby corrected as shown below:

In column 32, line 46 (Claim 39, line 46) before "when" delete "and".

In column 34, line 24 (Claim 45, line 24) before "when" delete "and".

Signed and Sealed this
Second Day of April, 2013

Teresa Stanek Rea
*Acting Director of the United States Patent and Trademark Office*